United States Patent
Ko et al.

(10) Patent No.: US 10,991,462 B2
(45) Date of Patent: Apr. 27, 2021

(54) SYSTEM AND METHOD OF CONTROLLING EXTERNAL APPARATUS CONNECTED WITH DEVICE

(71) Applicant: SAMSUNG ELECTRONICS CO., LTD., Suwon-si (KR)

(72) Inventors: Jae-woo Ko, Uiwang-si (KR); Hang-sik Shin, Yongin-si (KR); Se-jun Park, Seoul (KR); Yang-wook Kim, Hwaseong-si (KR); Hae-in Chun, Suwon-si (KR); Jae-ho Jung, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/780,301

(22) Filed: Feb. 3, 2020

(65) Prior Publication Data
US 2020/0177408 A1 Jun. 4, 2020

Related U.S. Application Data

(63) Continuation of application No. 15/654,829, filed on Jul. 20, 2017, now Pat. No. 10,567,189, which is a
(Continued)

(30) Foreign Application Priority Data

Sep. 10, 2012 (KR) .......................... 10-2012-0099739

(51) Int. Cl.
*H04B 1/00* (2006.01)
*G16H 40/67* (2018.01)
(Continued)

(52) U.S. Cl.
CPC ............. *G16H 40/67* (2018.01); *G08C 17/02* (2013.01); *H04L 12/2803* (2013.01);
(Continued)

(58) Field of Classification Search
CPC ... H04L 12/2803; H04L 67/303; G16H 40/67; G16H 50/20; G08C 17/02;
(Continued)

(56) References Cited

U.S. PATENT DOCUMENTS 7,764,180 B2  7/2010  Huang
8,660,530 B2  2/2014  Sharp et al.
(Continued)

FOREIGN PATENT DOCUMENTS

CN  1596029 A  3/2005
CN  101478403 A  7/2009
(Continued)

OTHER PUBLICATIONS

Communication dated Jun. 29, 2015 issued by the Australian Government IP Australia in counterpart Australian Patent Application No. 2013313760.
(Continued)

*Primary Examiner* — Naomi J Small
(74) *Attorney, Agent, or Firm* — Sughrue Mion, PLLC

(57) ABSTRACT

A mobile device includes a memory configured to store a program; and a processor configured to control one or more external apparatuses by executing the program. The program includes commands which, when executed by the processor, cause the processor to identify the one or more external apparatuses communicable with and controllable by the mobile device, from a plurality of external apparatuses; provide apparatus information of the one or more external apparatuses, to a server; receive, from the server, control information for controlling the one or more external apparatuses for a user's intention; and transmit a control command to the one or more external apparatuses based on the received control information.

15 Claims, 26 Drawing Sheets

Related U.S. Application Data continuation of application No. 14/679,749, filed on Apr. 6, 2015, now Pat. No. 9,722,811, which is a continuation-in-part of application No. 14/022,556, filed on Sep. 10, 2013, now Pat. No. 9,842,490.

(60) Provisional application No. 61/975,187, filed on Apr. 4, 2014.

(51) Int. Cl.
| | |
|---|---|
| *H04L 12/28* | (2006.01) |
| *G08C 17/02* | (2006.01) |
| *H04L 29/08* | (2006.01) |
| *A61B 5/00* | (2006.01) |
| *A61B 5/01* | (2006.01) |
| *A61B 5/024* | (2006.01) |
| *A61B 5/026* | (2006.01) |
| *G16H 50/20* | (2018.01) |

(52) U.S. Cl.
CPC .......... *H04L 67/303* (2013.01); *A61B 5/0022* (2013.01); *A61B 5/01* (2013.01); *A61B 5/026* (2013.01); *A61B 5/02438* (2013.01); *G08C 2201/21* (2013.01); *G08C 2201/42* (2013.01); *G08C 2201/93* (2013.01); *G16H 50/20* (2018.01)

(58) Field of Classification Search
CPC ............ G08C 2201/21; G08C 2201/42; G08C 2201/93; A61B 5/0022; A61B 5/01; A61B 5/02438; A61B 5/026; G06F 19/3418
USPC ........................................................ 340/5.82
See application file for complete search history.

(56) References Cited

U.S. PATENT DOCUMENTS

| | | | |
|---|---|---|---|
| 9,332,392 B1* | 5/2016 | Conway ................ | H04W 4/025 |
| 9,413,617 B2 | 8/2016 | Kim | |
| 2003/0001727 A1* | 1/2003 | Steinmark .............. | G08B 21/24 |
| | | | 340/309.16 |
| 2003/0003315 A1 | 1/2003 | Takahata et al. | |
| 2003/0187646 A1 | 10/2003 | Smyers et al. | |
| 2004/0066710 A1 | 4/2004 | Yuen et al. | |
| 2004/0256474 A1 | 12/2004 | Park et al. | |
| 2005/0121530 A1 | 6/2005 | Song | |
| 2006/0142968 A1 | 6/2006 | Han et al. | |
| 2006/0259201 A1 | 11/2006 | Brown | |
| 2008/0097908 A1 | 4/2008 | Dicks et al. | |
| 2009/0146779 A1* | 6/2009 | Kumar ............. | H04N 21/43615 |
| | | | 340/5.31 |
| 2009/0195349 A1 | 8/2009 | Frader-Thompson et al. | |
| 2009/0271002 A1 | 10/2009 | Asofsky | |
| 2010/0027967 A1 | 2/2010 | Yamada | |
| 2010/0069054 A1 | 3/2010 | Labidi et al. | |
| 2010/0100004 A1 | 4/2010 | van Someren | |
| 2010/0241699 A1 | 9/2010 | Muthukumarasamy et al. | |
| 2010/0279673 A1* | 11/2010 | Sharp ................... | H04L 67/125 |
| | | | 455/419 |
| 2011/0010014 A1 | 1/2011 | Oexman et al. | |
| 2011/0160802 A1 | 6/2011 | Rofougaran et al. | |
| 2011/0187864 A1 | 8/2011 | Snider | |
| 2012/0007295 A1 | 1/2012 | Howorth et al. | |
| 2012/0072951 A1* | 3/2012 | King ................... | H04L 41/0813 |
| | | | 725/37 |
| 2012/0127012 A1 | 5/2012 | Gicklhorn et al. | |
| 2012/0137436 A1 | 6/2012 | Andrienko | |
| 2012/0139703 A1 | 6/2012 | Szoke et al. | |
| 2012/0200497 A1 | 8/2012 | Nasiri et al. | |
| 2012/0221713 A1 | 8/2012 | Shin | |
| 2012/0226981 A1 | 9/2012 | Clavin | |
| 2013/0035077 A1 | 2/2013 | Tsai | |
| 2013/0063042 A1 | 3/2013 | Bora et al. | |
| 2013/0160141 A1 | 6/2013 | Tseng et al. | |

FOREIGN PATENT DOCUMENTS

| | | |
|---|---|---|
| JP | 2009110300 A | 5/2009 |
| KR | 20030027920 A | 4/2003 |
| KR | 10-2004-0019746 A | 3/2004 |
| KR | 10-2005-0045698 A | 5/2005 |
| KR | 10-2012-0072445 A | 7/2012 |
| KR | 10-1764210 B1 | 8/2017 |
| RU | 2006123259 A | 1/2008 |
| RU | 119473 U1 | 8/2012 |

OTHER PUBLICATIONS

Communication dated Apr. 18, 2016, issued by the Federal Service on Intellectual Property in counterpart Russian Patent Application No. 2015108021.
Communication issued by the State Intellectual Property Office of P.R. China dated Aug. 1, 2017 in counterpart Chinese Patent Application No. 201380047103.7.
Communication dated Mar. 8, 2018, issued by the State Intellectual Property Office of the People's Republic of China in counterpart Chinese Patent Application No. 201380047103.7.
Communication, dated Dec. 13, 2013, issued by the European Patent Office in counterpart European Patent Application No. 13183694.2.
International Search Report (PCT/ISA/210), dated Jan. 16, 2014, issued by the International Searching Authority in counterpart International Patent Application No. PCT/KR2013/008143.
Ruta, Michele, et al., "An Agent Framework for Knowledge-based Homes," ATES 2012, XP-002716710, Jun. 5, 2012, 8 pages, http://www.ates2012.org/papers/paper5.pdf.
Written Opinion (PCT/ISA/237), dated Jan. 16, 2014, issued by the International Searching Authority in counterpart International Patent Application No. PCT/KR2013/008143.
Communication dated May 25, 2020 issued by the Brazilian Intellectual Property Office in counterpart Brazilian Application No. BR112015004796-3.
Communication dated Feb. 24, 2021, by the Chinese National Intellectual Property Administration in counterpart Chinese Application No. 201910106708.8.
Communication dated Jan. 5, 2021, by the Chinese National Intellectual Property Administration in counterpart Chinese Application No. 201910106706.9.

\* cited by examiner

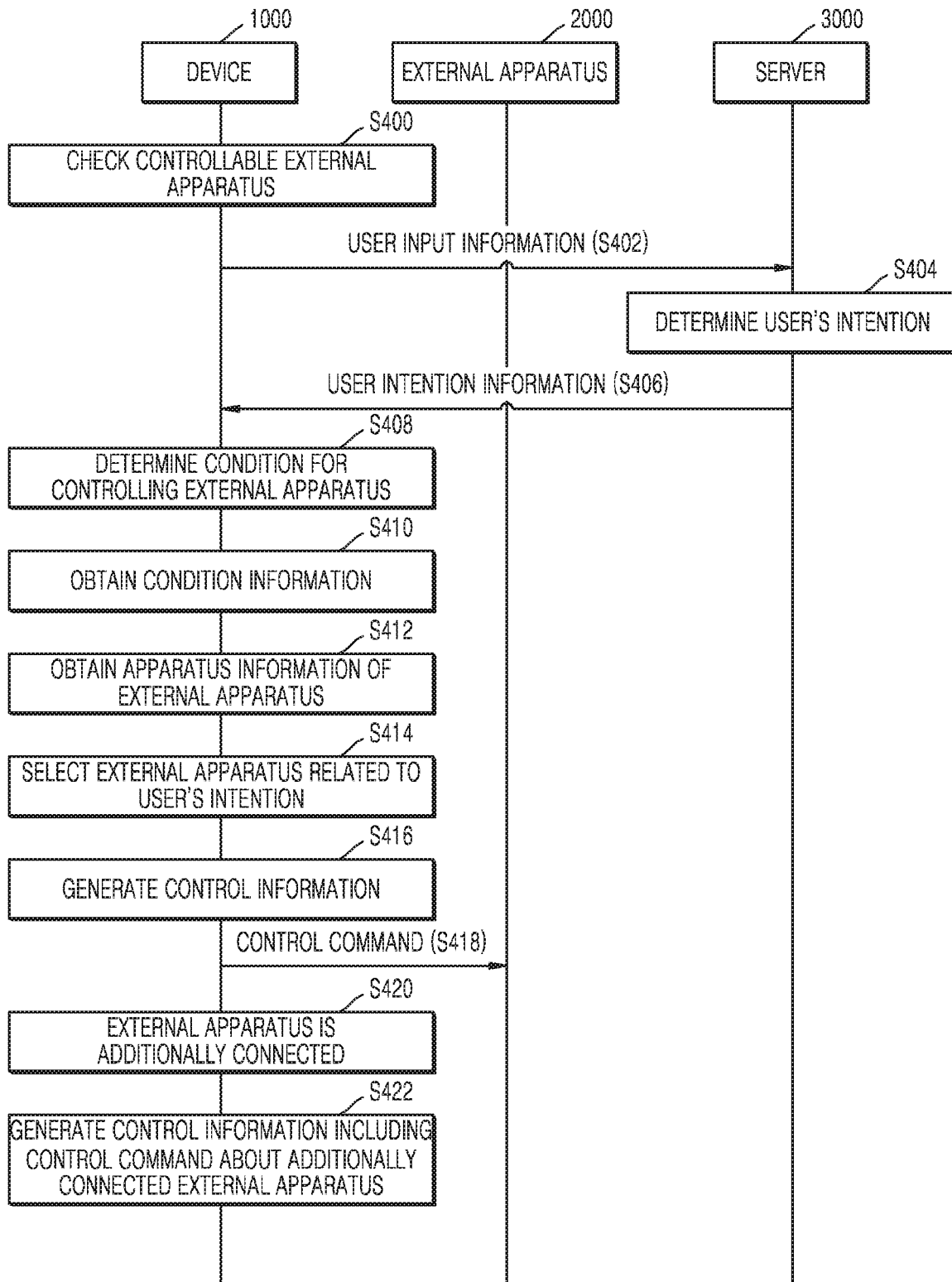

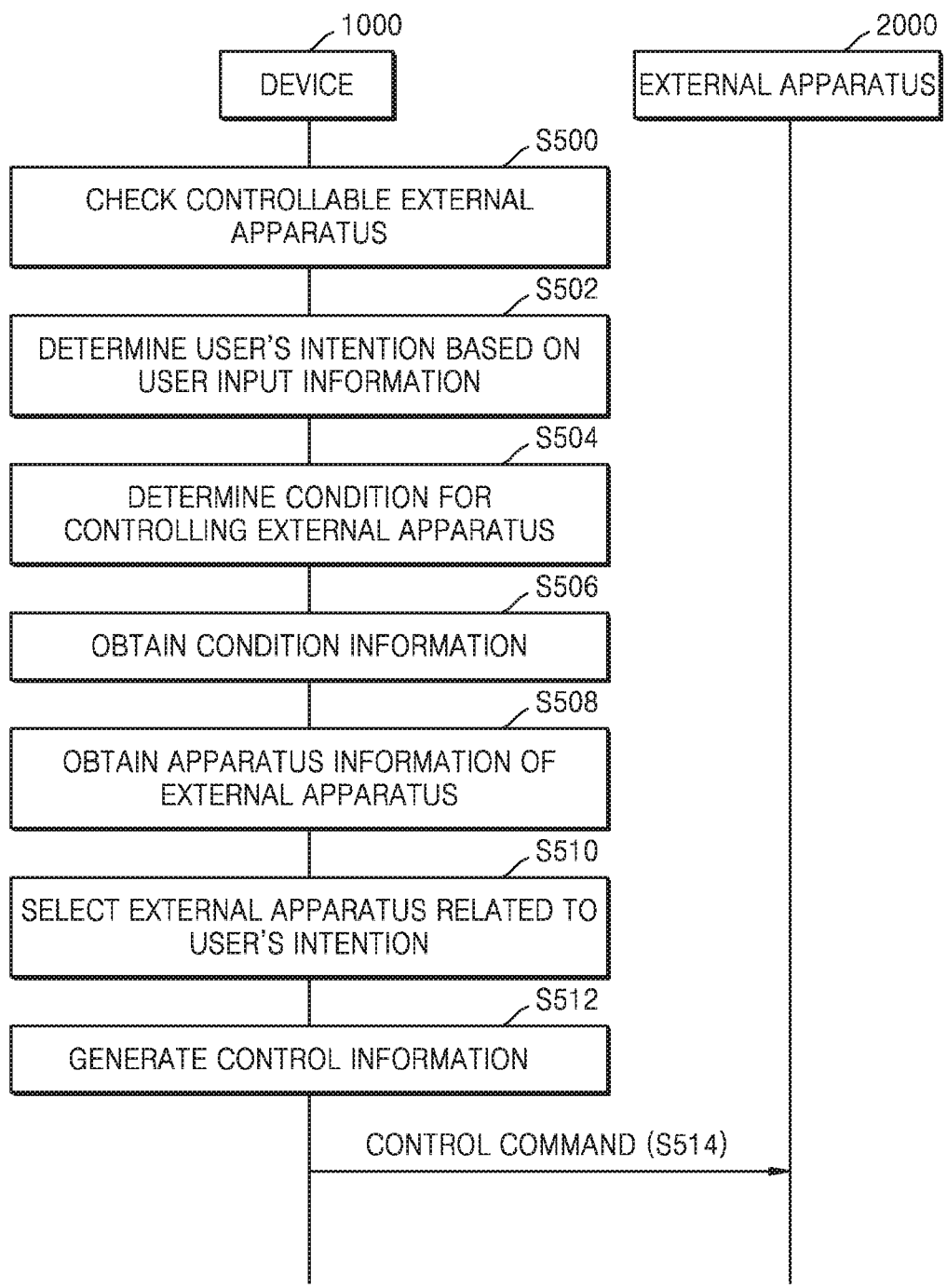

FIG. 6

| User Input Information (60) | User's Intention (62) | External Apparatus Controlling Condition (64) | Operation (66) |
|---|---|---|---|
| Wake me up at 7:00 if it doesn't rain tomorrow | When: tomorrow, 7:00<br>Condition: if it doesn't rain<br>Do: wake me up | Who: x<br>What: weather<br>When: tomorrow<br>Condition: sunny, cloudy<br>Where: device location | check time<br>check device location<br>check weather<br>output alarm information |
| Let's go home if the traffic is not heavy before 20:00 tomorrow | When: tomorrow, before 20:00<br>Condition: if the traffic is not heavy<br>Do: let's go home | Who: x<br>What: traffic<br>When: tomorrow, before 20:00<br>Condition: light traffic<br>Where: from device location to home | check time<br>check traffic from device location to home<br>start an engine<br>output route guidance information |
| Give me a video call if the baby wakes up | Condition: if the baby wakes up<br>Do: give me a video call | Who: baby<br>What: x<br>When: x<br>Condition: wakes up<br>where: x | obtain image captured inside house<br>obtain voice data inside house<br>check state of baby<br>make a video call |
| ... | ... | ... | ... |

| USER VOICE COMMAND (120) | BIOMETRIC INFORMATION OBTAINER (121) | CONDITION INFORMATION (122) | BIOMETRIC INFORMATION (123) | CONDITION FOR CONTROLLING EXTERNAL APPARATUS (124) | OPERATION (125) | CONTROL TARGET APPARATUS (126) |
|---|---|---|---|---|---|---|
| I'LL BE BACK WITHIN 30 MINUTES | MOBILE PHONE, SMART BAND | TEMPERATURE IN HOUSE, LOCATION INFORMATION OF DEVICE | HEART RATE, CALORIE CONSUMPTION | HEART RATE: GREATER THAN 120BMP, CALORIE CONSUMPTION: 500KCAL MOVING DISTANCE: GREATER THAN 3KM, | AIR CONDITIONER POWER ON, SET TEMPERATURE TO 18°C | AIR CONDITIONER |
| TURN ON THE AIR CONDITIONER | MOBILE PHONE, GLOVE, RING | TEMPERATURE IN HOUSE, LOCATION INFORMATION OF DEVICE | BLOOD FLOW RATE AT END OF HAND, CALORIE CONSUMPTION | BLOOD FLOW RATE AT END OF HAND: GREATER THAN REFERENCE VALUE CALORIE CONSUMPTION: 500KCAL MOVING DISTANCE: GREATER THAN 3KM, SENSIBLE TEMPERATURE OF USER: GREATER THAN 35°C | AIR CONDITIONER POWER ON, SET TEMPERATURE TO 18°C | AIR CONDITIONER |

FIG. 15

| USER VOICE COMMAND (150) | USER HEALTH STATE (151) | CONDITION INFORMATION (152) | CONDITION FOR CONTROLLING EXTERNAL APPARATUS (153) | OPERATION (154) | CONTROL TARGET APPARATUS (155) |
|---|---|---|---|---|---|
| I'LL BE BACK HOME WITHIN 30 MINUTES | ASTHMA | TEMPERATURE, HUMIDITY IN HOUSE, LOCATION INFORMATION OF DEVICE | LOCATION OF USER: NEAR HOME | AIR PURIFIER POWER ON | AIR PURIFIER |
| I'LL BE BACK HOME WITHIN 30 MINUTES | ATOPY | TEMPERATURE, HUMIDITY IN HOUSE, WEATHER, SEASON | TEMPERATURE IN HOUSE: GREATER THAN 30°C, HUMIDITY IN HOUSE: LESS THAN 50% | AIR CONDITIONER POWER ON, SET TEMPERATER OF AIR CONDITIONER TO 27°C, DEHUMIDIFIER POWER ON, SET HUMIDITY LEVEL OF DEHUMIDIFIER TO 55% | AIR CONDITIONER, DEHUMIDIFIER |
| I'LL BE BACK HOME WITHIN 30 MINUTES | ALLERGIC RHINITIS | TEMPERATURE, HUMIDITY IN HOUSE, WEATHER, SEASON | TEMPERATURE IN HOUSE: GREATER THAN 15°C, HUMIDITY IN HOUSE: LESS THAN 30% | HEATER POWER ON, SET TEMPERATURE TO 20°C, DEHUMIDIFIER POWER ON, SET HUMIDITY LEVEL OF DEHUMIDIFIER TO 40% | HEATER, DEHUMIDIFIER |

SYSTEM AND METHOD OF CONTROLLING EXTERNAL APPARATUS CONNECTED WITH DEVICE

CROSS-REFERENCE TO RELATED PATENT APPLICATIONS

This application is a continuation of U.S. patent application Ser. No. 15/654,829, filed Jul. 20, 2017, which is a continuation of U.S. patent application Ser. No. 14/679,749, filed Apr. 6, 2015 (now U.S. Pat. No. 9,722,811), which claims the benefit of U.S. Provisional Application No. 61/975,187, filed Apr. 4, 2014, and is a continuation-in-part of U.S. patent application Ser. No. 14/022,556, filed Sep. 10, 2013 (now U.S. Pat. No. 9,842,490), which claims priority from Korean Patent Application No. 10-2012-0099739, filed Sep. 10, 2012, in the Korean Intellectual Property Office. The disclosures of the above-named applications are incorporated herein in their entireties by reference.

BACKGROUND

1. Field

Apparatuses and methods consistent with exemplary embodiments relate to controlling an external apparatus connected with a device according to a user's intention.

2. Description of the Related Art

Due to development of natural language analysis technologies and mobile technologies, a device may analyze information input by a user and may operate according to the user's intention. However, even though a device may be able to operate according to a user's intention, it is difficult for the device to utilize various connectable or device-compliant apparatuses. As such, it is difficult to control a device by effectively reflecting various true intentions of a user.

Accordingly, there is a need for methods and apparatuses for obtaining various types of condition information by using a device and an external apparatus connectable with the device and for operating the device and different external apparatuses by effectively reflecting various intentions of a user.

SUMMARY

Exemplary embodiments may address at least the above problems and/or disadvantages and other disadvantages not described above. The exemplary embodiments are not required to overcome the disadvantages described above, and an exemplary embodiment may not overcome any of the problems described above.

One or more of exemplary embodiments provide a system and method of controlling an external apparatus connected with a device by determining a user's intention based on user input information, and controlling the device and the external apparatus according to the user's intention.

According to an aspect of an exemplary embodiment, there is provided a server configured to control at least one external apparatus, the server including: a communicator configured to receive an input command of a user and biometric information of the user from a device; and a controller configured to determine a condition for controlling the at least one external apparatus and operation of the at least one external apparatus based on the received input command of the user and the received biometric information of the user, and provide a control command for controlling the operation of the at least one external apparatus to the at least one external apparatus if the determined condition is satisfied.

According to another aspect of an exemplary embodiment, there is provided a method of controlling at least one external apparatus, the method including: receiving an input command of a user and biometric information of the user from a device; and determining a condition for controlling the at least one external apparatus and operation of the at least one external apparatus based on the received input command of the user and the received biometric information of the user; and providing a control command for controlling the operation of the at least one external apparatus to the at least one external apparatus if the determined condition is satisfied.

According to another aspect of an exemplary embodiment, there is provided a server configured to control at least one external apparatus, the server including: a communicator configured to receive an input command of a user and biometric information of the user from a device; and a controller configured to determine a condition for controlling the at least one external apparatus and operation of the at least one external apparatus based on the received input command of the user and the received biometric information of the user, and provide a control command for controlling the operation of the at least one external apparatus to the at least one external apparatus if the determined condition is satisfied.

According to another aspect of an exemplary embodiment, there is provided a method of controlling at least one external apparatus, the method including: receiving an input command of a user and biometric information of the user from a device; and determining a condition for controlling the at least one external apparatus and operation of the at least one external apparatus based on the received input command of the user and the received biometric information of the user; and providing a control command for controlling the operation of the at least one external apparatus to the at least one external apparatus if the determined condition is satisfied.

According to another aspect of an exemplary embodiment, there is provided a non-transitory computer-readable recording medium having recorded thereon a computer program which, when executed by a computer system, performs the method.

According to another aspect of an exemplary embodiment, there is provided a non-transitory computer-readable recording medium having recorded thereon a computer program which, when executed by a computer system, performs the method.

BRIEF DESCRIPTION OF THE DRAWINGS

The above and/or other aspects will become more apparent by describing certain exemplary embodiments, with reference to the accompanying drawings, in which:

FIG. 4 is a flowchart of a method of controlling an external apparatus by a device, according to an exemplary embodiment;

FIG. 5 is a flowchart of a method of controlling an external apparatus by a device, according to an exemplary embodiment;

FIG. 6 is an operation table, according to an exemplary embodiment;

FIG. 12 is a schematic diagram showing an example of an operation table of a device for controlling an external apparatus based on biometric information, according to one or more exemplary embodiments;

FIG. 15 is a schematic diagram showing an example of an operation table of a device for controlling an external apparatus based on a health state of a user, according to one or more exemplary embodiments;

DETAILED DESCRIPTION

Figure 1:
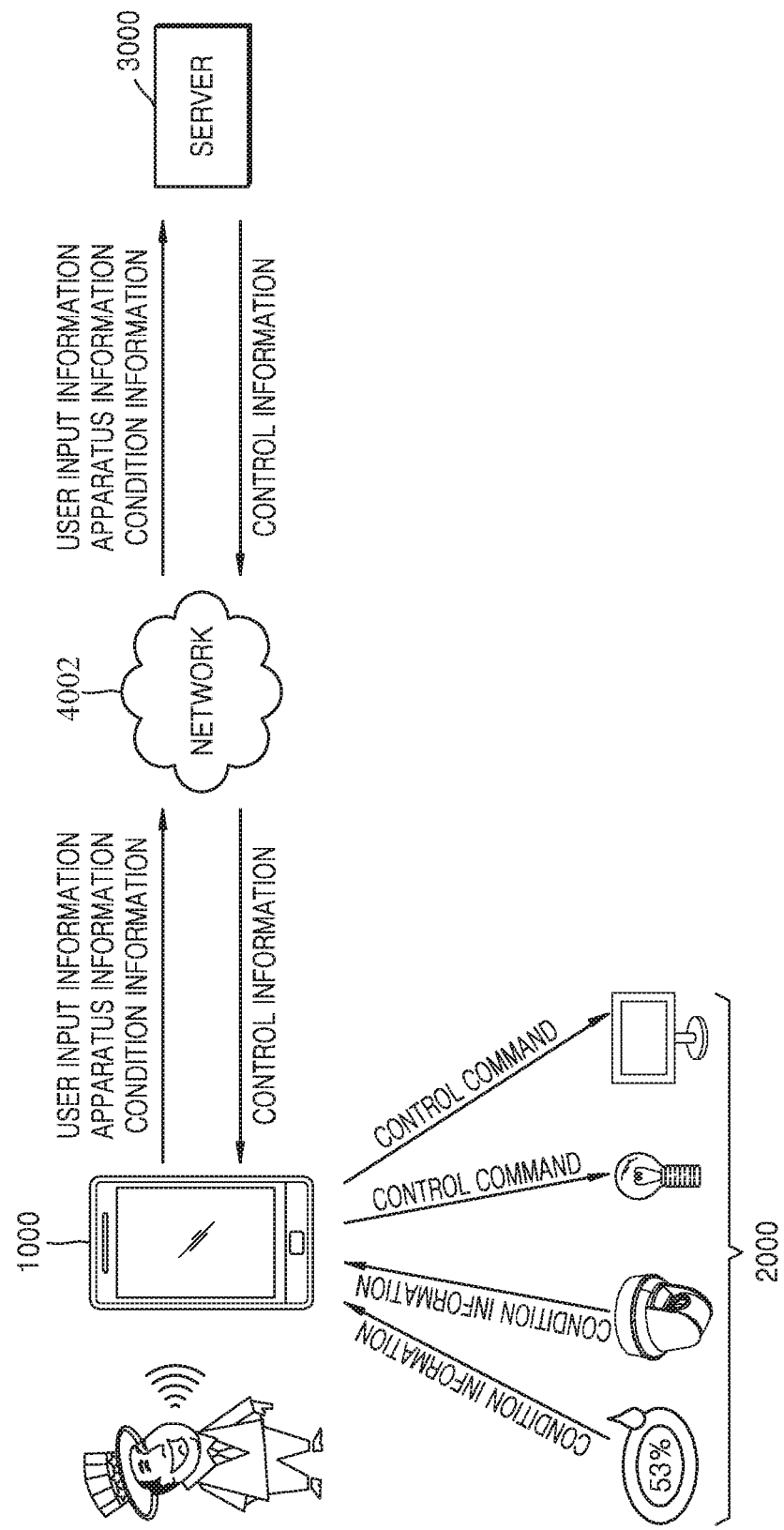
FIG. 1 is an overall schematic diagram of a system for controlling an external apparatus via a device, according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Throughout the specification, it should be understood that when an element is referred to as being "connected with" another element, it can be directly connected with the other element, or electrically connected with the other element while intervening elements may also be present. Also, when a part "includes" or "comprises" an element, unless there is a particular description contrary thereto, the part can further include other elements, not excluding the other elements.

Expressions such as "at least one of," when preceding a list of elements, modify the entire list of elements and do not modify the individual elements of the list.

FIG. 1 is an overall schematic diagram of a system for controlling an external apparatus via a device, according to an exemplary embodiment.

As illustrated in FIG. 1, the system includes the device 1000, one or more external apparatuses 2000 connected with the device 1000, a server 3000, and a network 4002.

Referring to FIG. 1, the device 1000 may generate user input information based on a user input, and may provide the user input information, apparatus information of the external apparatus 2000, and condition information to the server 3000 such that the external apparatus 2000 may be controlled according to a user's intention.

The device 1000 may receive a text input or a voice input of the user, may generate the user input information based on the received input, and may provide the generated user input information to the server 3000. The device 1000 may check the external apparatus 2000 connectable with the device 1000, and may obtain and provide the apparatus information of the external apparatus 2000 to the server 3000. Furthermore, the device 1000 may obtain the condition information via the device 1000 or the external apparatus 2000, and may provide the obtained condition information to the server 3000. The device 1000 may obtain the condition information based on control information to be described below, but is not limited thereto.

The server 3000 may analyze the user's intention based on the user input information, and may generate and provide the control information to the device 1000 such that the device 1000 may operate according to the user's intention and that the external apparatus 2000 may be controlled by the device 1000. The server 3000 may determine the user's intention by analyzing the user input information, and may determine a condition for controlling the external apparatus 2000 in such a way that the user's intention is satisfied. The server 3000 may check whether the determined condition is satisfied and may generate the control information for controlling operations of the device 1000 and the external apparatus 2000.

The device 1000 may receive the control information from the server 3000, and may transmit a control command to some external apparatuses 2000 based on the control information.

The device 1000 is an apparatus capable of transmitting and receiving information to and from the server 3000 and of transmitting the control command to the external apparatus 2000, and may be, for example, a smartphone, a mobile phone, a personal digital assistant (PDA), a laptop computer, a media player, a global positioning system (GPS) apparatus, or another mobile or non-mobile computing apparatus, but is not limited thereto.

The external apparatus 2000 may be an apparatus connectable with and controllable by the device 1000, and/or capable of at least partially sharing functions provided by the device 1000. The external apparatus 2000 may be a stand-alone apparatus capable of independently executing an application, but is not limited thereto. The external apparatus 2000 may include an input apparatus, an output apparatus, or a control apparatus, for example, a home appliance such as a smart TV or an air conditioner, a security camera, a recorder, a mobile phone, a personal computer (PC), a pillow vibrator, a motor vehicle, a navigator, a microphone, a speaker, a pedal, a joystick, a musical instrument (e.g., a piano, an organ, an electronic keyboard, a guitar, a violin, or a cello), a game manipulator, a doll, a medical appliance, sporting equipment, a camera, or a sensor.

The server 3000 may be a service providing server for providing the control information for allowing the device 1000 to control the external apparatus 2000 according to the user's intention, but is not limited thereto.

The server 3000 may be a cloud server, for example, a PC of the user. If the server 3000 is a cloud server, the server 3000 may include a predetermined intelligence engine, may analyze the user's intention via the intelligence engine, and may transmit the control information for controlling the external apparatus 2000 to the device 1000. Otherwise, if the server 3000 is a client server, the server 3000 may receive predetermined information from a separate service providing server (e.g., a weather information providing server or a traffic information providing server).

The network 4002 may be implemented as a wired network such as a local area network (LAN), a wide area network (WAN), or a value added network (VAN), or a wireless network such as a mobile radio communication network, a near field communication (NFC) network, or a satellite communication network. The network 4002 may be a comprehensive data communication network for allowing appropriate communications between the network components illustrated in FIG. 1, and may include wired Internet, wireless Internet, and/or a mobile wireless communication network.

Figure 2:
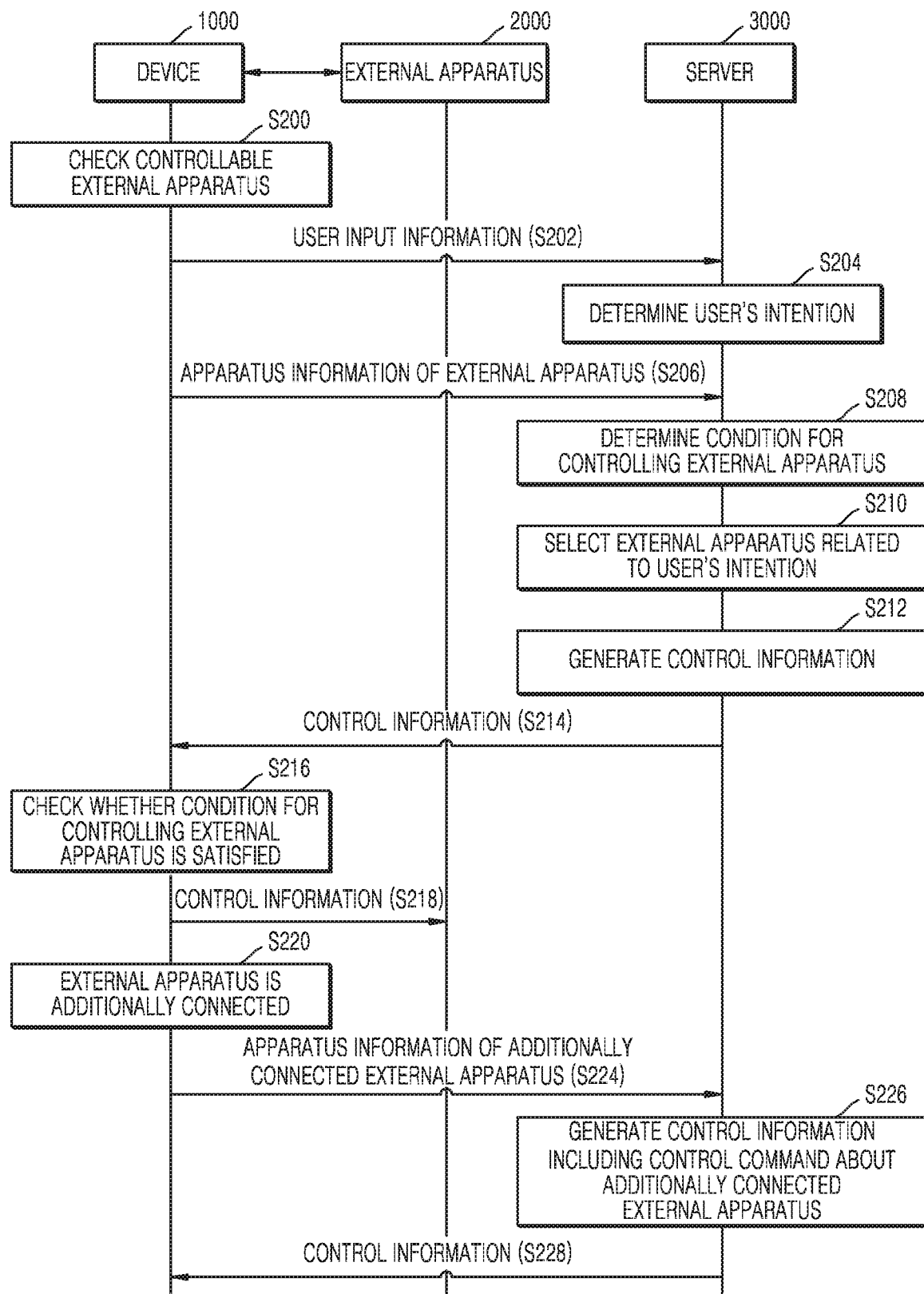
FIG. 2 is a flowchart of a method of controlling an external apparatus by a device, according to an exemplary embodiment.

FIG. 2 is a flowchart of a method of controlling the external apparatus 2000 by the device 1000 based on control information generated by the server 3000, according to an exemplary embodiment.

In operation S200, the device 1000 checks the external apparatus 2000 controllable by the device 1000. The device 1000 may check the external apparatus 2000 controllable by the device 1000 from among the external apparatuses 2000 connectable with the device 1000. The controllable external apparatus 2000 may be an external apparatus connected or connectable with the device 1000 and having installed therein a predetermined application for utilizing a control service according to an exemplary embodiment. If the application is not installed in the controllable external apparatus 2000, the device 1000 may perform communication connection and pairing with the external apparatus 2000, and may provide to the external apparatus 2000 the application or link information for downloading the application.

The external apparatus 2000 may include, for example, a home appliance such as a smart TV or an air conditioner, a security camera, a recorder, a mobile phone, a PC, a pillow vibrator, a motor vehicle, or a navigator, but is not limited thereto. The device 1000 and the external apparatus 2000 may be connected with each other via a wired network such as a LAN, a WAN, or a VAN, or a wireless network such as a mobile radio communication network, an NFC network, or a satellite communication network. The device 1000 may be connected with the external apparatus 2000 via, for example, a home gateway (not shown).

The device 1000 may receive from the checked external apparatus 2000 apparatus information of the external apparatus 2000, but is not limited thereto. The device 1000 may receive the apparatus information of the external apparatus 2000 from a separate server (not shown). For example, if the device 1000 is connected with the external apparatus 2000 via a home gateway (not shown), the device 1000 may request the home gateway for the apparatus information of the external apparatus 2000. The apparatus information of the external apparatus 2000 may include information about at least one of an identification value of the external apparatus 2000, a media access control (MAC) address, a service set identifier (SSID), the type of the external apparatus 2000, capability provided by the external apparatus 2000, a category, and a command used to control the external apparatus 2000. The capability provided by the external apparatus 2000 may include, for example, a voice output capability, a video output capability, a voice recording capability, an image capturing capability, and a humidity sensing capability, but is not limited thereto.

After user input information is generated in operation S202 or a user's intention is determined in operation S204, the device 1000 may search for the external apparatus 2000 to be controlled by the device 1000, based on the user input information or the user's intention.

In operation S202, the device 1000 provides the user input information to the server 3000. The device 1000 may generate the user input information based on a user input, and may provide the generated input information to the server 3000. The user input information may be information about at least one of text input by the user, a voice of the user, a facial expression of the user, a gesture of the user, and a physical state of the user.

If the user inputs text to the device 1000, the device 1000 may provide the text data input by the user as the user input information to the server 3000. For example, if the user inputs text such as "Wake me up at 7:00 if it doesn't rain tomorrow" to the device 1000, the device 1000 may provide the input text data as the user input information to the server 3000. Otherwise, if the user inputs a voice to the device 1000, the device 1000 may provide the input voice data as the user input information to the server 3000. The device 1000 may transform the input voice data into text data, and may transmit the transformed text data as the user input information to the server 3000. Alternatively, for example, the device 1000 may generate the user input information by using an email or a text message stored in the device 1000.

The device 1000 may parse the user input information, and may transmit the parsed data to the server 3000. If the user input information is text data, the device 1000 may parse the text data. Otherwise, if the user input information is voice data, the device 1000 may transform the voice data into text data and may parse the transformed text data. However, an exemplary embodiment is not limited thereto. The device 1000 may provide a voice data file to the server 3000, and the server 3000 may transform and parse the received voice data file into text.

In operation S204, the server 3000 determines the user's intention based on the user input information. The server 3000 may determine the user's intention by analyzing the user input information. In order to analyze received text data as the user input information, the server 3000 may use various natural language analysis methods. For example, the server 3000 may analyze the text data by using natural language processing such as morpheme analysis, syntax analysis, or named entity recognition. Alternatively, the server 3000 may determine the user's intention based on the user input information by using, for example, ontology-based reasoning and probability-based reasoning. If the server 3000 receives voice data as the user input information, the server 3000 may transform the received voice data into text data, and may analyze the transformed text data. The server 3000 may generate user intention information by analyzing the user input information. For example, if the user input information is "Wake me up at 7:00 if it doesn't rain tomorrow", the server 3000 may generate the user intention information including time information such as "tomorrow, 7:00", information related to condition information such as "if it doesn't rain", and operation information such as "wake me up". The information related to condition information may be information used by the device 1000 or the server 3000 to obtain condition information about the user's intention.

Alternatively, the server 3000 may determine the user's intention via an interactive interface using feedback. For example, if the user's intention is not easily determined based on the user input information received from the device 1000, the server 3000 may request the device 1000 for additional user input information. The server 3000 may notify additionally needed information to the device 1000. The server 3000 may determine the user's intention by using the user input information additionally received from the device 1000. For example, if user input information such as "Give me a call if the baby wakes up" is received from the device 1000, the server 3000 may request the device 1000 to additionally provide information about a point of time when the baby wakes up. The device 1000 may additionally provide user input information such as "Give me a call if the baby wakes up tomorrow morning" to the server 3000, and the server 3000 may determine the user's intention based on the additionally received user input information.

In operation S206, the device 1000 provides the apparatus information of the checked external apparatus 2000 to the server 3000. The device 1000 may provide information about at least one of an identification value of the external apparatus 2000, a MAC address, an SSID, the type of the external apparatus 2000, capability provided by the external apparatus 2000, a category, and a command used to control the external apparatus 2000 to the server 3000. In operation S206, the device 1000 may provide the apparatus information of the device 1000 to the server 3000. The apparatus information of the device 1000 may include information about at least one of, for example, an identification value of the device 1000, a MAC address, an SSID, the type of the device 1000, capability provided by the device 1000, a category, and a command used to control the device 1000.

In operation S208, the server 3000 determines a condition for controlling the external apparatus 2000 based on the user's intention. The condition for controlling the external apparatus 2000 is a condition for allowing a user-desired operation to be performed according to the user's intention. For example, if the user input information is "Wake me up if it doesn't rain at 7:00 tomorrow", a condition such as "if it doesn't rain at 7:00 tomorrow" for a user-desired operation such as "wake me up" may be the condition for controlling the external apparatus 2000. The server 3000 may determine a condition that has to be satisfied to control operation of the external apparatus 2000 or the device 1000, based on the user intention information. For example, if the user intention information includes time information such as "tomorrow, 7:00" and information related to condition information such as "if it doesn't rain", the server 3000 may determine a time condition such as "tomorrow", a weather condition such as "sunny, cloudy", and a place condition such as "device location" as the condition for controlling the external apparatus 2000. In order to ensure that the determined condition is satisfied, a predetermined external apparatus 2000 may be controlled.

In operation S210, the server 3000 selects the external apparatus 2000 related to the user's intention. The server 3000 may select the external apparatus 2000 related to the user's intention, based on operation information included in the user intention information and the apparatus information received from the device 1000. For example, if the user intention information includes operation information such as "wake me up", the server 3000 may select the external apparatus 2000 to wake up the user, by using the apparatus information received from the device 1000. The server 3000 may select, for example, a pillow vibrator and/or a lighting device as the external apparatuses 2000 for waking up the user.

In operation S212, the server 3000 generates control information for satisfying the user's intention. The control information may include information for checking whether the condition determined by the server 3000 is satisfied, and information for controlling operation of at least one of the device 1000 and the selected external apparatus 2000 if the condition determined by the server 3000 is satisfied. The control information may include a control command for controlling operation of the device 1000 or the external apparatus 2000, and information to generate the control command.

In more detail, the server 3000 may generate the control information for checking whether the condition determined by the server 3000 is satisfied, based on the condition determined by the server 3000 and the apparatus information received from the device 1000. For example, if the condition determined by the server 3000 includes a time condition such as "tomorrow", a weather condition such as "sunny, cloudy", and a place condition such as "device location", the server 3000 may generate the control information for checking whether the condition determined by the server 3000 is satisfied by allowing the device 1000 to check the date, the location of the device 1000, and the weather via the device 1000 or the external apparatus 2000. The control information may include a control command instructing to check the date and the weather, a control command instructing to obtain humidity information from a humidity sensor, and a command instructing to check the location of the device 1000, and the control commands included in the control information may be aligned in a predetermined order.

However, the control information is not limited thereto and may omit a control command but may include information referred to so as to generate a control command, for example, "determine whether the weather is sunny or cloudy at a device location tomorrow".

If the condition determined by the server 3000 is satisfied, the server 3000 may generate the control information for operating the device 1000 or the external apparatus 2000. The server 3000 may generate the control information for operating the device 1000 or the external apparatus 2000, based on the operation information included in the user intention information and the apparatus information received from the device 1000. For example, if the user intention information includes operation information such as "wake me up", the server 3000 may generate a control command instructing the device 1000 to output alarm information, a control command instructing a lighting device to be turned on, and/or a control command instructing a pillow vibrator to generate vibration.

The control information may include a plurality of control commands for controlling operation of at least one of the device 1000 and the external apparatus 2000, and the plurality of control commands may be executed in a predetermined order by at least one of the device 1000 and the external apparatus 2000.

In operation S214, the server 3000 provides the generated control information to the device 1000.

In operation S216, the device 1000 checks whether the condition for controlling the external apparatus 2000 is satisfied. The device 1000 may check whether the condition determined by the server 3000 is satisfied, based on the control information received from the server 3000. If the control information received from the server 3000 includes a control command for checking whether the condition for controlling the external apparatus 2000 is satisfied, the device 1000 may operate according to the control command included in the control information to check whether the condition is satisfied. Otherwise, if the control information received from the server 3000 does not include the control command for checking whether the condition for controlling the external apparatus 2000 is satisfied, the device 1000 may generate a control command based on the control information, and may check whether the condition is satisfied, according to the generated control command.

In operation S218, the device 1000 provides the control command to the external apparatus 2000 based on the control information. The device 1000 may transmit the control command to the external apparatus 2000 in order to follow the user's intention if the condition for controlling the external apparatus 2000 is satisfied. If the condition for controlling the external apparatus 2000 is satisfied, the device 1000 may transmit the control commands for operating the external apparatuses 2000 to the external apparatuses 2000 in a predetermined order. The device 1000 may perform a predetermined operation based on the control information.

In operation S220, another external apparatus (not shown) is additionally connected with the device 1000 and, in operation S224, the device 1000 provides apparatus information of the additionally connected external apparatus to the server 3000.

In operation S226, the server 3000 generates control information including a control command about the additionally connected external apparatus. The server 3000 may change the control information for satisfying the user's intention, based on the apparatus information of the additionally connected external apparatus.

In operation S228, the server 3000 provides the changed control information to the device 1000. As such, the device 1000 may control operation of the device 1000 or the external apparatus 2000 based on the changed control information.

Figure 3:
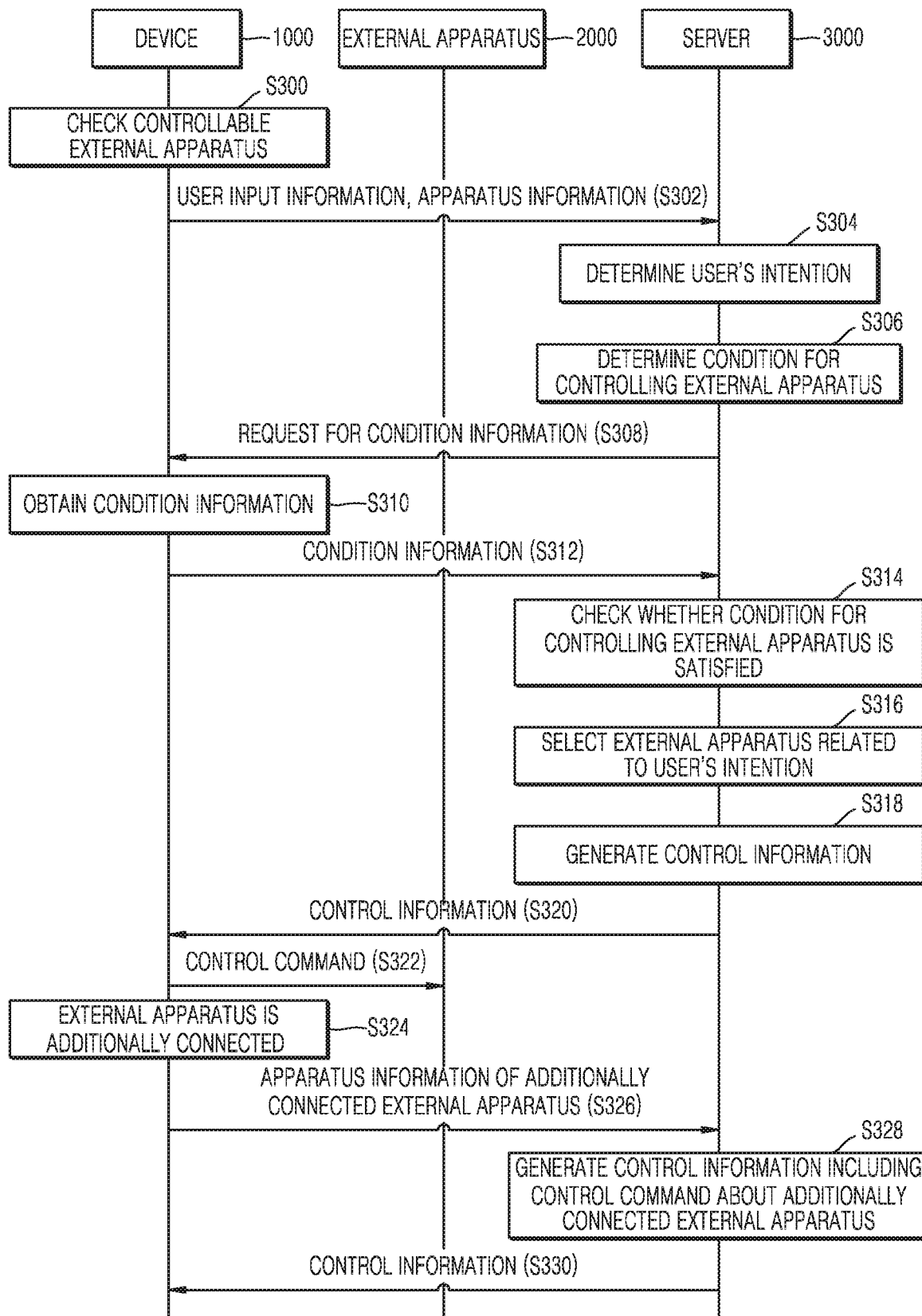
FIG. 3 is a flowchart of a method of controlling an external apparatus by a device, according to an exemplary embodiment.

FIG. 3 is a flowchart of a method of controlling the external apparatus 2000 by the device 1000 based on control information generated by the server 3000, according to an exemplary embodiment. In FIG. 3, the server 3000 may check whether a condition for controlling the external apparatus 2000 is satisfied. Since some of the operations of FIG. 3 are similar to those described above with reference to FIG. 2, the detailed description thereof is omitted.

In operation S300, the device 1000 checks the external apparatus 2000 controllable by the device 1000.

In operation S302, the device 1000 provides user input information and the apparatus information to the server 3000. The device 1000 may generate the user input information based on a user input, and may provide the generated input information to the server 3000.

Also, the device 1000 may provide information about at least one of an identification value of the external apparatus 2000, the type of the external apparatus 2000, and a command used to control the external apparatus 2000 to the server 3000.

In operation S304, the server 3000 determines the user's intention based on the user input information. The server 3000 may determine the user's intention by analyzing the user input information. In order to analyze received text data as the user input information, the server 3000 may use various natural language analysis methods. For example, the server 3000 may analyze the text data by using natural language processing such as morpheme analysis, syntax analysis, or named entity recognition. If the server 3000 receives voice data as the user input information, the server 3000 may transform the received voice data into text data, and may analyze the transformed text data. Also, the server 3000 may generate user intention information by analyzing the user input information.

In operation S306, the server 3000 determines a condition for controlling the external apparatus 2000 based on the user's intention. The server 3000 may determine a condition that has to be satisfied to control operation of the external apparatus 2000 or the device 1000, based on the user intention information. For example, if the user intention information includes time information such as "tomorrow, 7:00" and information related to condition information such as "if it doesn't rain", the server 3000 may determine a time condition such as "tomorrow", a weather condition such as "sunny, cloudy", and a place condition such as "device location" as the condition for controlling the external apparatus 2000.

In operation S308, the server 3000 requests the device 1000 for condition information. The server 3000 may request the device 1000 for the condition information obtainable by the device 1000 and the condition information obtainable by the external apparatus 2000, based on the condition information. The server 3000 may request the device 1000 for the condition information needed to check whether the determined condition is satisfied. For example, if a time condition, a weather condition, and a place condition are determined, the server 3000 may request the device 1000 to provide information about the weather at a fixed time at a fixed place as the condition information to the server 3000. The server 3000 may provide the type of the condition information to the device 1000, but is not limited thereto. The server 3000 may provide to the device 1000 a control command instructing the device 1000 and the external apparatus 2000 to obtain the condition information.

In operation S310, the device 1000 obtains the condition information. The device 1000 may obtain the condition information in response to a request to obtain the condition information. The device 1000 may obtain various types of the condition information from the external apparatus 2000 and a separate server (not shown). For example, the device 1000 may obtain location information of the device 1000 from a location information providing server (not shown), may obtain weather information around the device 1000 from a weather server (not shown), and may obtain traffic information about a predetermined route from a traffic information providing server (not shown).

Also, for example, the device 1000 may obtain humidity information from a humidity sensor (not shown), may obtain a captured image from a photographing apparatus (not shown), and may obtain recorded voice data from a recording apparatus (not shown). The device 1000 may obtain the condition information from an apparatus included in the device 1000. For example, the device 1000 may obtain various types of the condition information from a temperature sensor, a humidity sensor, a geomagnetic sensor, a gravity sensor, a motion sensor, a gyro sensor, a camera, and a recorder included in the device 1000. The device 1000 may obtain the condition information about a physical state of the user. The condition information about the physical state of the user may be, for example, information about a heart rate, an electrocardiogram (ECG), breathing, a pulse, and physical exercise of the user, and may be obtained from the device 1000 or the external apparatus 2000 connected with the device 1000. Furthermore, the device 1000 may obtain the condition information about a network status, a login status of the external apparatus 2000, an application installed in the device 1000 or the external apparatus 2000, and a user using the application. However, the device 1000 is not limited thereto and may obtain various types of information as the condition information.

In operation S312, the device 1000 provides the obtained condition information to the server 3000. The device 1000 may obtain the condition information in a preset cycle, and may provide the obtained condition information to the server 3000 in real time, but is not limited thereto. The server 3000 may obtain the condition information from another device (not shown) or another server (not shown).

In operation S314, the server 3000 checks whether the condition for controlling the external apparatus 2000 is satisfied, based on the condition information. The server 3000 may check whether the condition is satisfied, based on the condition information received from at least one of the device 1000, the other device, and the other server.

In operation S316, the server 3000 selects the external apparatus 2000 related to the user's intention. The server 3000 may check an operation for satisfying the user's intention, and may select the external apparatus 2000 for performing the checked operation. For example, if the user intention information includes operation information such as "wake me up", the server 3000 may select a lighting device and/or a pillow vibrator.

In operation S318, the server 3000 generates control information about the selected external apparatus 2000. If the condition determined by the server 3000 is satisfied, the server 3000 may generate the control information for operating the device 1000 or the external apparatus 2000. The server 3000 may generate the control information for operating the device 1000 or the external apparatus 2000, based on the operation information included in the user intention information and the apparatus information received from the device 1000. For example, if the user intention information includes operation information such as "wake me up", the server 3000 may generate a control command instructing the device 1000 to output alarm information, a control command instructing a lighting device to be turned on, and a control command instructing a pillow vibrator to generate vibration. The control commands included in the control information generated by the server 3000 may be aligned in a predetermined order.

In operation S320, the server 3000 provides the generated control information to the device 1000.

In operation S322, the device 1000 transmits the control command to the external apparatus 2000 based on the control information. The device 1000 may transmit the control commands for operating the external apparatuses 2000 to the external apparatuses 2000 in a predetermined order. The device 1000 may perform a predetermined operation based on the control information.

In operation S324, another external apparatus (not shown) is additionally connected with the device 1000 and, in operation S326, the device 1000 provides apparatus information of the additionally connected external apparatus to the server 3000.

In operation S328, the server 3000 generates control information including a control command about the additionally connected external apparatus. The server 3000 may change the control information for satisfying the user's intention, based on the apparatus information of the additionally connected external apparatus.

In operation S330, the server 3000 provides the changed control information to the device 1000. As such, the device 1000 may control operation of the device 1000 or the external apparatus 2000 based on the changed control information.

FIG. 4 is a flowchart of a method of generating a control command and controlling the external apparatus 2000 by the device 1000 based on user intention information received from the server 3000, according to an exemplary embodiment. In FIG. 4, the device 1000 may determine a condition for controlling the external apparatus 2000, based on the user intention information. Since some of the operations of FIG. 4 are similar to those described above with reference to FIGS. 2 and 3, the detailed description thereof is omitted.

In operation S400, the device 1000 checks the external apparatus 2000 controllable by the device 1000 and, in operation S402, the device 1000 provides user input information to the server 3000. In operation S404, the server 3000 determines a user's intention based on the user input information. Operations S400, S402, and S404 may respectively correspond to operations S200, S202, and S204.

In operation S406, the server 3000 provides user intention information to the device 1000. For example, if the user input information is "Wake me up at 7:00 if it doesn't rain tomorrow", the server 3000 may provide to the device 1000 the user intention information including time information such as "tomorrow, 7:00", condition information such as "if it doesn't rain", and operation information such as "wake me up".

In operation S408, the device 1000 determines a condition for controlling the external apparatus 2000 based on the user's intention. The device 1000 may decide a condition that has to be satisfied to control operation of the external apparatus 2000 or the device 1000, based on the user intention information. For example, if the user intention information includes time information such as "tomorrow, 7:00" and condition information such as "if it doesn't rain", the device 1000 may decide a time condition such as "tomorrow", a weather condition such as "sunny, cloudy", and a place condition such as "device location" as the condition for controlling the external apparatus 2000.

In operation S410, the device 1000 obtains condition information. The device 1000 may obtain various types of the condition information from the external apparatus 2000 and a separate server (not shown).

In operation S412, the device 1000 obtains apparatus information of the external apparatus 2000. The device 1000 may receive the apparatus information of the external apparatus 2000 from the external apparatus 2000, but is not limited thereto. The device 1000 may receive the apparatus information of the external apparatus 2000 from a separate server (not shown). For example, if the device 1000 is connected with the external apparatus 2000 via a home gateway (not shown), the device 1000 may request the home gateway for the apparatus information of the external apparatus 2000. The apparatus information of the external apparatus 2000 may include information about at least one of an identification value of the external apparatus 2000, the type of the external apparatus 2000, and a command used to control the external apparatus 2000.

In operation S414, the device 1000 selects the external apparatus 2000 related to the user's intention. The device 1000 may check an operation for satisfying the user's intention, and may select the external apparatus 2000 for performing the checked operation.

In operation S416, the device 1000 generates control information about the selected external apparatus 2000. If the condition determined by the device 1000 is satisfied, the device 1000 may generate the control information for operating the device 1000 or the external apparatus 2000. The device 1000 may generate the control information for operating the device 1000 or the external apparatus 2000, based on the operation information included in the user intention information and the apparatus information received from the device 1000. The control information may include control commands about at least one external apparatus 2000 and the device 1000, and the control commands may be aligned in a predetermined order.

In operation S418, the device 1000 provides a predetermined control command to the external apparatus 2000 based on the generated control information.

In operation S420, another external apparatus (not shown) is additionally connected with the device 1000 and, in operation S422, the device 1000 generates control information including a control command about the additionally connected external apparatus. The device 1000 may change the control information for satisfying the user's intention, based on apparatus information of the additionally connected external apparatus. As such, the device 1000 may control operation of the device 1000 or the external apparatus 2000 based on the changed control information.

FIG. 5 is a flowchart of a method of directly determining a user's intention and controlling the external apparatus 2000 by the device 1000 based on user input information, according to an exemplary embodiment.

In operation S500, the device 1000 checks the external apparatus 2000 controllable by the device 1000.

In operation S502, the device 1000 determines a user's intention based on user input information. The device 1000 may determine the user's intention by analyzing the user input information. In order to analyze the user input information, the device 1000 may use various natural language analysis methods. For example, the device 1000 may analyze text data as the user input information by using natural language processing such as morpheme analysis, syntax analysis, or named entity recognition. If the user input information is voice data, the device 1000 may transform the voice data into text data, and may analyze the transformed text data. The device 1000 may generate user intention information by analyzing the user input information. For example, if the user input information is "Wake me up at 7:00 if it doesn't rain tomorrow", the device 1000 may generate the user intention information including time information such as "tomorrow, 7:00", condition information such as "if it doesn't rain", and operation information such as "wake me up".

In operation S504, the device 1000 determines a condition for controlling the external apparatus 2000 based on the user's intention and, in operation S506, the device 1000 obtains condition information. In operation S508, the device 1000 obtains apparatus information of the external apparatus 2000, in operation S510, the device 1000 selects the external apparatus 2000 related to the user's intention and, in operation S512, the device 1000 generates control information about the selected external apparatus 2000. In operation S514, the device 1000 provides a predetermined control command to the external apparatus 2000 based on the generated control information.

Operations S504, S506, S508, S510, S512, and S514 may correspond to the operations described above with reference to FIGS. 2, 3, and 4, and thus, are not described in detail again.

FIG. 6 is an operation table of the device 1000 for controlling the external apparatus 2000, according to an exemplary embodiment. Information about operation of the device 1000 in relation to user input information is recorded in the operation table of the device 1000.

As illustrated in FIG. 6, the operation table 58 of the device 1000 may include a user input information field 60, a user's intention field 62, an external apparatus controlling condition field 64, and an operation field 66. The operation table of the device 1000 may be generated by at least one of the device 1000 and the server 3000.

User input information obtained by the device 1000 is recorded in the user input information field 60. If a user inputs text to the device 1000, the text data input by the user may be recorded in the user input information field 60. If the user input information is voice data, the voice data may be transformed into text data, and the transformed text data may be stored in the user input information field 60.

The user input information recorded in the user input information field 60 may include, for example, "Wake me up at 7:00 if it doesn't rain tomorrow", "Let's go home if the traffic is not heavy before 20:00 tomorrow", and "Give me a video call if the baby wakes up".

Information about a user's intention determined based on the user input information may be recorded in the user's intention field 62. The user input information may be analyzed by using natural language processing such as morpheme analysis, syntax analysis, or named entity recognition. For example, if the user input information is "Wake me up at 7:00 if it doesn't rain tomorrow", "When: tomorrow, 7:00, Condition: if it doesn't rain, Do: wake me up" may be recorded in the user's intention field 62.

Information about a condition that has to be satisfied to control the external apparatus 2000 according to the user's intention may be recorded in the external apparatus controlling condition field 64.

For example, based on the information recorded in the user's intention field 62, the external apparatus controlling condition field 64 may contain "Who: x, What: weather, When: tomorrow, Condition: sunny, cloudy, Where: device location". That is, a subject condition such as "weather", a time condition such as "tomorrow", a weather condition such as "sunny, cloudy", and a place condition such as "device location" may be recorded in the external apparatus controlling condition field 64. In addition to "Who", "What", "When", "Condition", and "Where", various condition items may be further included in the external apparatus controlling condition field 64. If predetermined data is not recorded as a condition item, the server 3000 may request the device 1000 for additional user input information about the condition item having no recorded data, and may receive the additional user input information from the device 1000 to record predetermined data as the condition item. That is, if the user's intention is not determined based on the user input information, or if a condition and operation for controlling the external apparatus 2000 according to the user's intention are not determined, the server 3000 may request the device 1000 for additional user input information.

The device 1000 may generate a control command for checking whether a predetermined condition is satisfied, based on the information recorded in the condition field 64.

Operation information of the device 1000 and the external apparatus 2000 for determining whether the condition for controlling the external apparatus 2000 is satisfied, and for operating the device 1000 and the external apparatus 2000 according to the user's intention may be recorded in the operation field 66.

For example, based on the information recorded in the user's intention field 62, "check time", "check device location", and "check weather" may be recorded in the operation field 66. If the condition for controlling the external apparatus 2000 is satisfied, as an operation of the device 1000 and the external apparatus 2000, "output alarm information" may be recorded in the operation field 66.

Based on the operation information recorded in the operation field 66, control information of the device 1000 and the external apparatus 2000 for performing the operation recorded in the operation field 66 may be generated. The control information may include a plurality of control commands for controlling operation of at least one of the device 1000 and the external apparatus 2000, and the plurality of control commands may be executed by at least one of the device 1000 and the external apparatus 2000 in a predetermined order. For example, based on "check time", "check device location" and "check weather" recorded in the operation field 66, a control command may be generated in such a way that the device 1000 checks the time, the location of the device 1000, and the weather by using at least one of the device 1000, a separate server (not shown), and the external apparatus 2000. For example, based on "output alarm information" recorded in the operation field 66, a control command may be generated in such a way that the device 1000 and the external apparatus 2000 output predetermined alarm information.

Although the device 1000 determines the user's intention and determines the condition and operation for controlling the external apparatus 2000 in the above description, exemplary embodiments are not limited thereto. The determining of the condition and operation for controlling the external apparatus 2000 based on the user input information by the device 1000 may be included in the determining of the user's intention.

Figure 7:
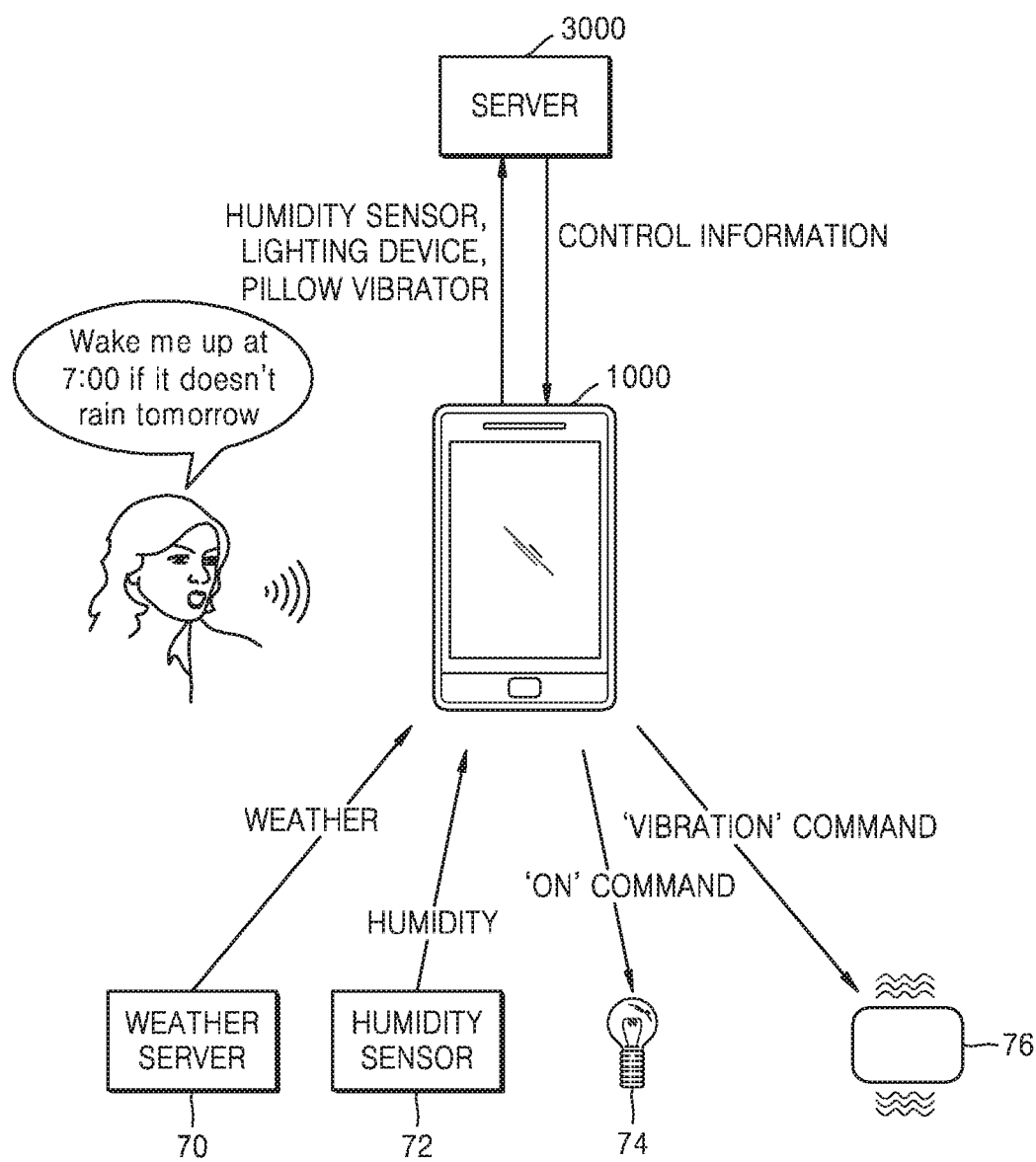
FIG. 7 is a schematic diagram of controlling an external apparatus, according to an exemplary embodiment.

FIG. 7 is a schematic diagram showing that the external apparatus 2000 is controlled according to user input information that is input to the device 1000, in a system for controlling the external apparatus 2000, according to an exemplary embodiment.

Referring to FIG. 7, if a user inputs voice data such as "Wake me up at 7:00 if it doesn't rain tomorrow" to the device 1000, the device 1000 may provide the voice data or text data transformed from the voice data, as user input information to the server 3000. The device 1000 may provide apparatus information of a humidity sensor 72, a lighting device 74, and a pillow vibrator 76 connectable with the device 1000, to the server 3000.

The server 3000 may determine the user's intention based on the user input information, and may determine a condition for controlling the external apparatus 2000. The server 3000 may determine whether the determined condition is satisfied, may generate control information for controlling the device 1000 and the external apparatus 2000, and may provide the generated control information to the device 1000.

The device 1000 may determine whether the condition is satisfied, by obtaining weather information from a weather server 70 based on the received control information, and obtaining humidity information from the humidity sensor 72. If the condition is satisfied, the device 1000 may transmit a control command instructing to power on to the lighting device 74 and/or may transmit a control command instructing to generate vibration to the pillow vibrator 76.

Figure 8:
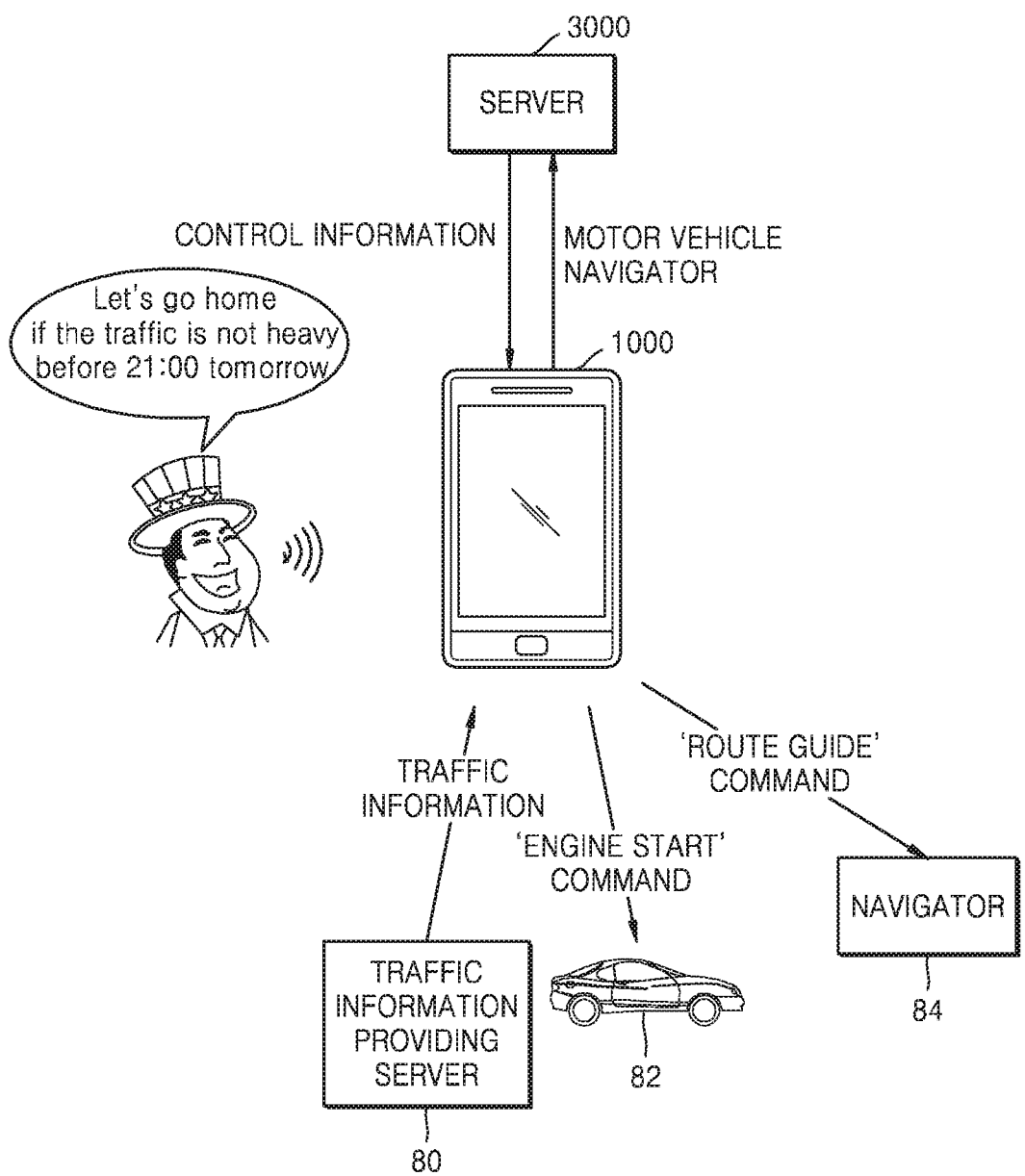
FIG. 8 is a schematic diagram of controlling an external apparatus, according to an exemplary embodiment.

FIG. 8 is a schematic diagram showing that the external apparatus 2000 is controlled according to user input information that is input to the device 1000, in a system for controlling the external apparatus 2000, according to an exemplary embodiment.

Referring to FIG. 8, if a user inputs voice data such as "Let's go home if the traffic is not heavy before 21:00 tomorrow" to the device 1000, the device 1000 may provide the voice data or text data transformed from the voice data, as user input information to the server 3000. The device 1000 may provide apparatus information of a motor vehicle 82 and a navigator 84 connectable with the device 1000, to the server 3000.

The server 3000 may determine the user's intention based on the user input information, and may determine a condition for controlling the external apparatus 2000. The server 3000 may determine whether the determined condition is satisfied, may generate control information for controlling the device 1000 and the external apparatus 2000, and may provide the generated control information to the device 1000.

The device 1000 may determine whether the condition is satisfied, by obtaining traffic information about a route from a current location of the device 1000 to home, from a traffic information providing server 80 based on the received control information. If the condition is satisfied, the device 1000 may transmit a control command instructing to start an engine to the motor vehicle 82 and may transmit a control command instructing to output route guidance information to the navigator 84.

Figure 9:
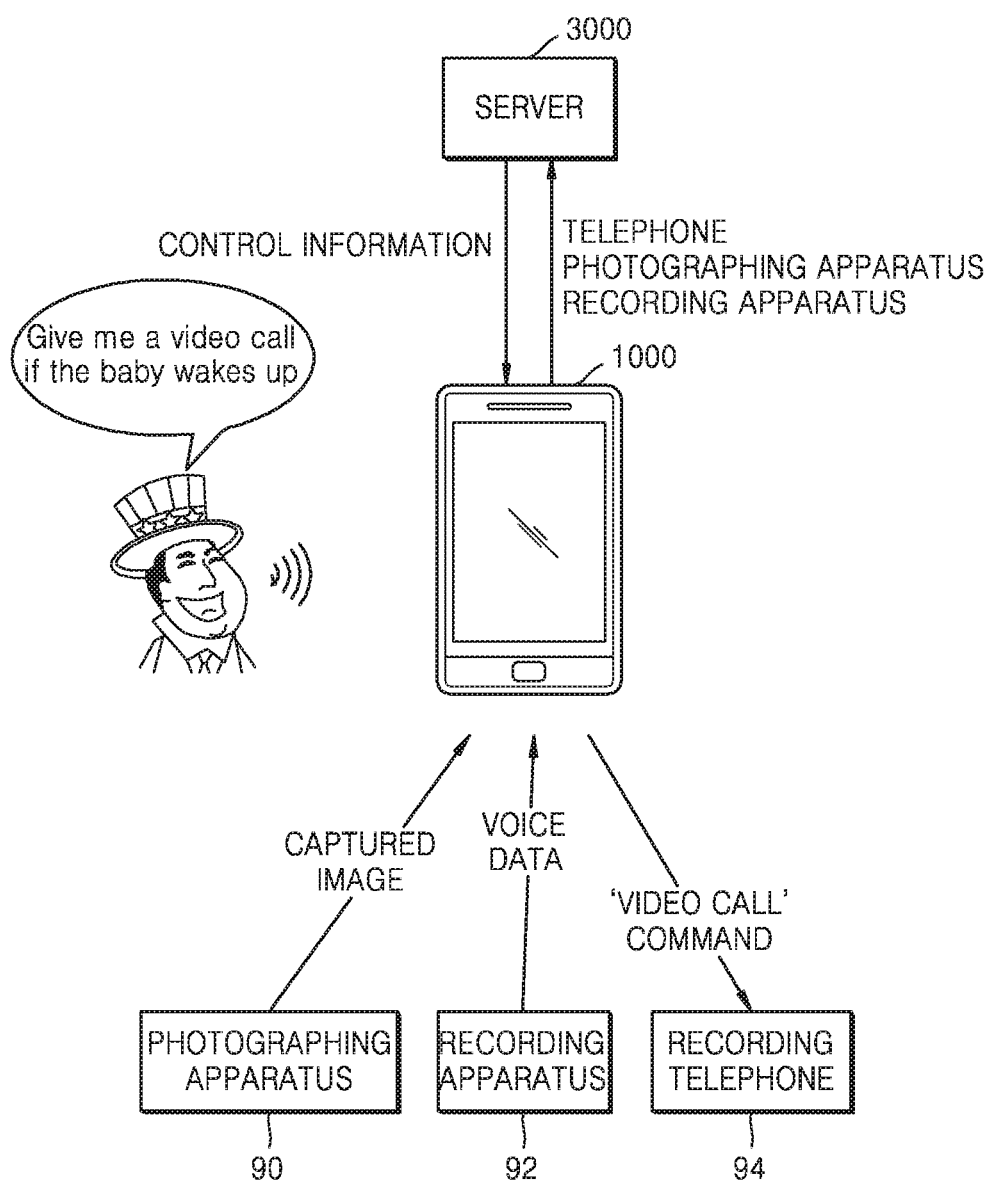
FIG. 9 is a schematic diagram of controlling an external apparatus, according to an exemplary embodiment.

FIG. 9 is a schematic diagram showing that the external apparatus 2000 is controlled according to user input information that is input to the device 1000, in a system for controlling the external apparatus 2000, according to an exemplary embodiment.

Referring to FIG. 9, if a user inputs voice data such as "Give me a video call if the baby wakes up" to the device 1000, the device 1000 may provide the voice data or text data transformed from the voice data, as user input information to the server 3000. The device 1000 may provide apparatus information of a photographing apparatus 90, a recording apparatus 92, and a telephone 94 connectable with the device 1000, to the server 3000.

The server 3000 may determine the user's intention based on the user input information, and may determine a condition for controlling the external apparatus 2000. The server 3000 may determine whether the determined condition is satisfied, may generate control information for controlling the device 1000 and the external apparatus 2000, and may provide the generated control information to the device 1000.

The device 1000 may determine whether the condition is satisfied, by obtaining a captured image from the photographing apparatus 90 and obtaining recorded voice data from the recording apparatus 92 based on the received control information. If the condition is satisfied, the device

1000 may transmit a control command instructing to make a video call to the telephone 94.

Figure 10:
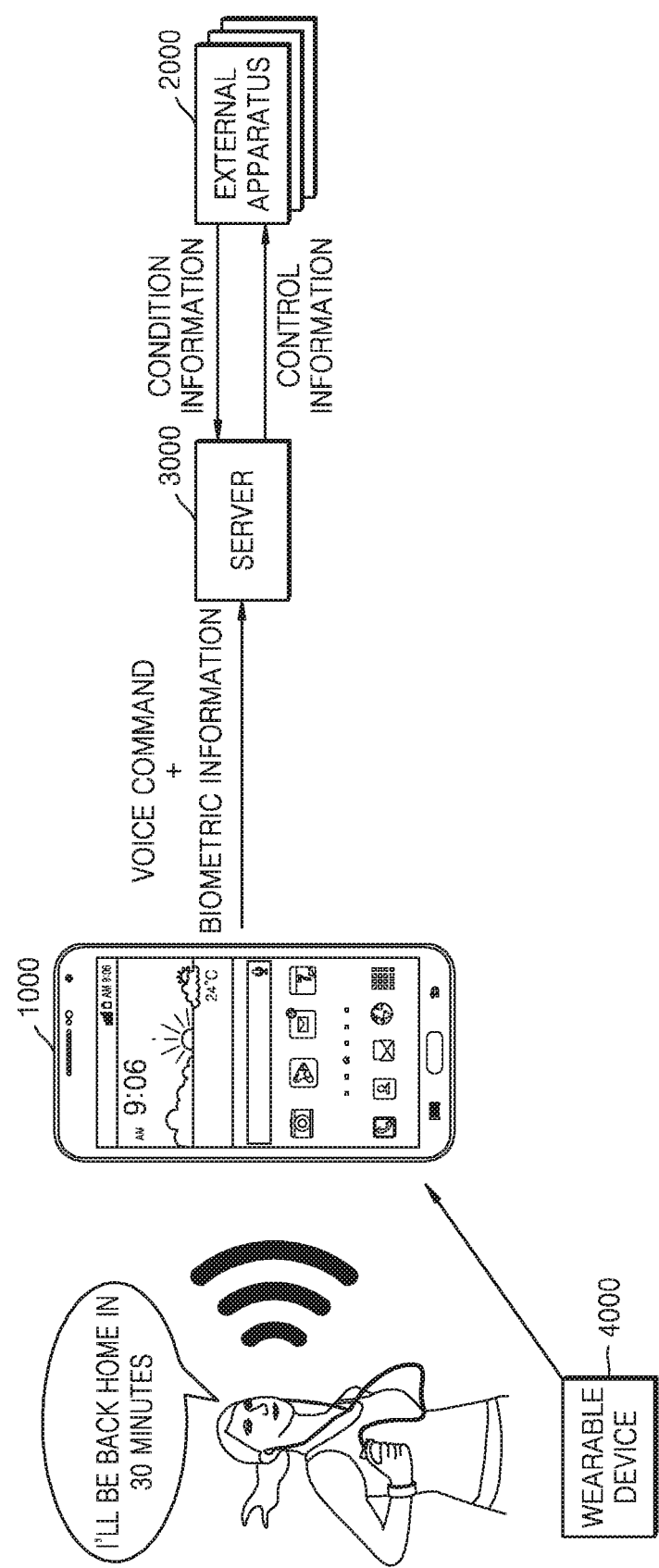
FIG. 10 is a schematic diagram of controlling an external apparatus based on a voice command and biometric information of a user, which is performed by a server, according to one or more exemplary embodiments.

FIG. 10 is a schematic diagram showing controlling of the external apparatus 2000 based on a voice command and biometric information of a user, which is performed by the server 3000, according to one or more exemplary embodiments.

Referring to FIG. 10, while the user of the device 1000 is jogging, the user may input a voice command to the device 1000. Then, the device 1000 may receive the voice command input by the user and obtain biometric information of the user from a wearable device 4000. In this case, the wearable device 4000 may be a device separate from the device 1000 or a device included in the device 1000. Additionally, the device 1000 may transmit the voice command and the biometric information to the server 3000.

The server 3000 may receive the voice command and the biometric information from the device 1000, and receive condition information from the external apparatus 2000. In this case, the external apparatus 2000 may be, for example, an apparatus located in a house of a user.

Then, the server 3000 may generate a control command for controlling the external apparatus 2000 in consideration of the voice command of the user, the biometric information of the user, and a condition of the external apparatus 2000, and transmit the generated control command to the external apparatus 2000. Thus, the device 1000 may control the external apparatus 2000 according to the voice command of the user in consideration of a biometric state of the user.

For example, the server 3000 may pre-store reference values of pieces of biometric information for determining a state of the user. If the user inputs a voice command to the device 1000, the wearable device 4000 may sense biometric information of the user and provide the biometric information to the server 3000. Additionally, the server 3000 may determine a state of the user by comparing a piece of biometric information of the user to a reference value and analyzing whether a difference between the piece of biometric information and the reference value is equal to or greater than a certain value within a certain range (for example, whether a heart rate is equal to or greater than 30 bpm, whether a difference between a sensible temperature and a current temperature is greater than ±5° C., or the like). The server 3000 may determine an intention of the user in consideration of the voice command of the user and the state of the user. The server 3000 may select the external apparatus 2000 which is a control target so as to satisfy the intention of the user, and determine operation of the selected external apparatus 2000. Additionally, the server 3000 may generate control information for controlling the external apparatus 2000 and transmit the generated control information to the external apparatus 2000.

If information for selecting the external apparatus 2000 is included in the voice command of the user (for example, if the user says "turn on an air conditioner"), the server 3000 may select the external apparatus 2000, specified by the voice command, as a control target. The server 3000 may determine the state of the user as well as the biometric information of the user, in consideration of information received from the device 1000 or the external apparatus 2000. For example, the server 3000 may determine that the state of the user is "hot", based on information regarding a heart rate of the user, calories consumed by the user, and a distance the user has jogged. Additionally, the server 3000 may select an air conditioner as a control target, generate control information for setting a set temperature of the air conditioner as 18° C. and transmit the control information to the air conditioner.

Additionally, for example, if the user inputs a voice command saying "I'll be back home within 30 minutes" to the device 1000, the wearable device 4000 may transmit biometric information of the user to the server 3000. The server 3000 may determine that a sensible temperature of the user is 35° C. (which is a state of the user) by using the received biometric information. Additionally, the server 3000 may select an air conditioner at home as a control target, and generate control information for setting a set temperature of the air conditioner as 18° C.

If the user feels cold when the user is back home and changes the set temperature of the air conditioner to 22° C., the air conditioner may transmit the temperature changed by the user to the server 3000. The server 3000 may change a setting for operation of the air conditioner according to a condition for controlling the air conditioner, by using information about the temperature changed by the user. The server 3000 may change a set value for 'setting a set temperature of the air conditioner to 18° C. when a sensible temperature is 35° C.' to a set value for 'changing a set temperature of the air conditioner to 22° C. when a sensible temperature is 35° C.'. Then, if a sensible temperature of the user is 35° C. when the user inputs a voice command saying "I'll be back home within 30 minutes", the server 3000 may generate a control command instructing the air conditioner to set a temperature to 22° C., instead of a control command instructing the air conditioner to set a temperature to 18° C.

Figure 11:
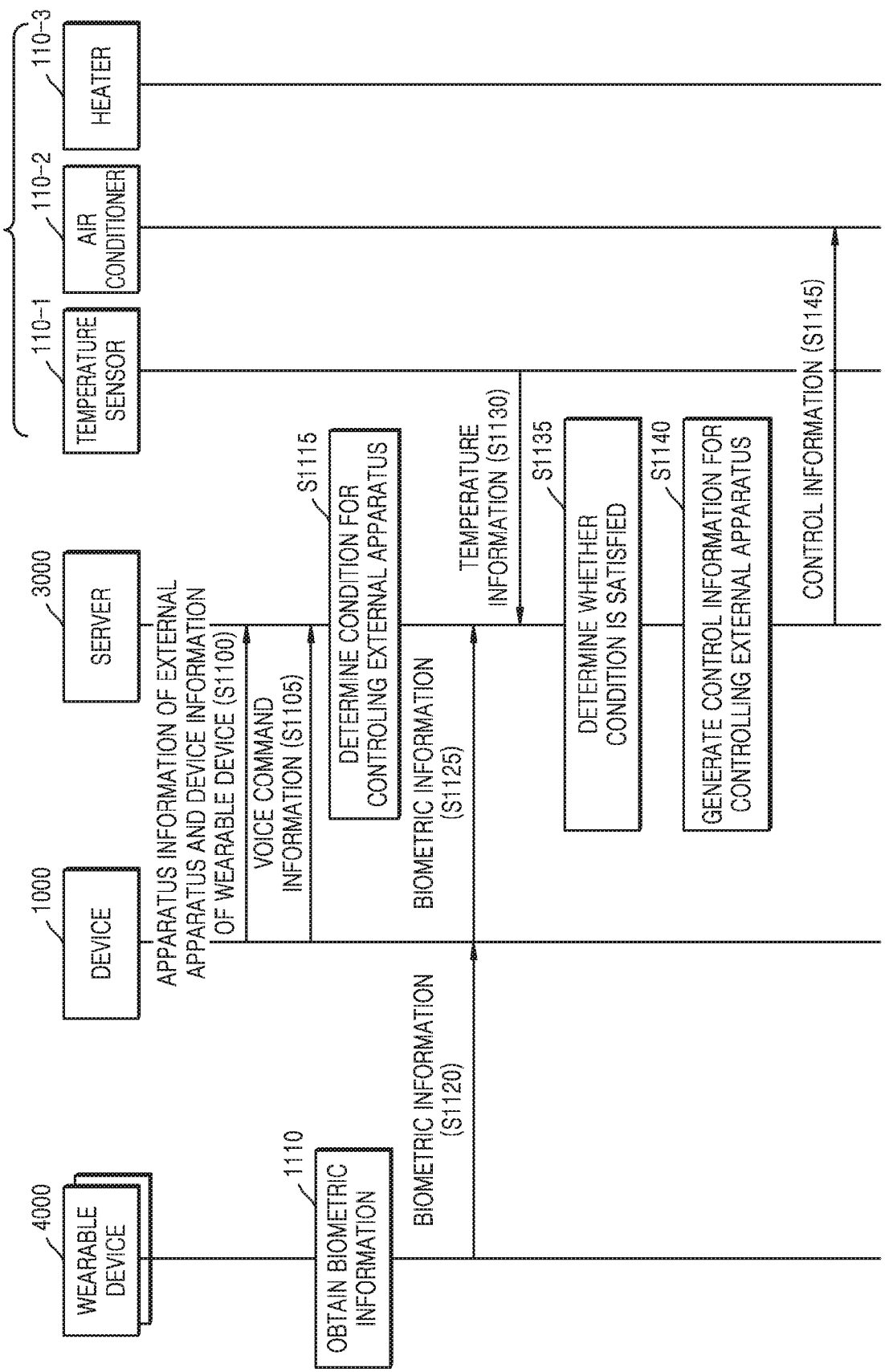
FIG. 11 is a detailed flowchart of a method of controlling an external apparatus according to a voice command of a user in consideration of biometric information of the user, which is performed by a server, according to one or more exemplary embodiments.

FIG. 11 is a detailed flowchart of a method of controlling the external apparatus 2000 according to a voice command of a user in consideration of biometric information of the user, which is performed by the server 3000, according to one or more exemplary embodiments.

In operation S1100, the device 1000 may provide apparatus information of the external apparatus 2000 and device information of the wearable device 4000 to the server 3000. The device 1000 provides the apparatus information of the external apparatus 2000, located inside or outside a house of the user, to the server 3000. The external apparatus 2000 may include, for example, a home appliance such as a smart TV or an air conditioner, a security camera, a recorder, a mobile phone, a PC, a pillow vibrator, a motor vehicle, a navigator, a microphone, a speaker, a pedal, a joystick, a musical instrument (e.g., a piano, an organ, an electronic keyboard, a guitar, a violin, or a cello), a game manipulator, a doll, a medical appliance, sporting equipment, a camera, or a sensor, but is not limited thereto. The apparatus information of the external apparatus 2000 may include information about at least one selected from the group consisting of an identification value of the external apparatus 2000, a MAC address, an SSID, a type of the external apparatus 2000, a capability provided by the external apparatus 2000, a category, and a command used to control the external apparatus 2000.

Additionally, the device 1000 may provide the device information of the wearable device 4000 worn by the user to the server 3000. The wearable device 4000 may include, for example, a smart watch, smart glasses, a smart band, a smart earphone, smart shoes, a smart ring, a smart bracelet, or a smart necklace. The device information of the wearable device 4000 may, for example, include information about at least one selected from the group consisting of an identification value of the wearable device 4000, a MAC address, an SSID, a type of the wearable device 4000, a capability provided by the wearable device 4000, a category, and a command used to control the wearable device 4000.

The apparatus information of the external apparatus 2000 and the device information of the wearable device 4000, provided to the server 3000 by the device 1000, may be used for the server 3000 to set a condition for controlling the external apparatus 2000.

In operation S1105, the device 1000 may provide voice command information to the server 3000. The device 1000 may record a voice command of the user, and transmit the recorded voice command to the server 3000. However, the providing of the voice command information is not limited thereto. The device 1000 may convert the recorded voice command into text and provide the text, obtained by the converting, to the server 3000. For example, the device 1000 may provide information indicating a voice command of the user such as "I'll be back home within 30 minutes" or 'turn on an air conditioner' to the server 3000.

In operation S1105, the device 1000 is described as recording a voice command and transmitting the recorded voice command to the server 3000. However, embodiments are not limited thereto. The wearable device 4000 may record a voice command of the user, and transmit the recorded voice command to the device 1000. Then, the device 1000 may transmit the recorded voice command to the server 3000. Alternatively, the wearable device 4000 may record a voice command and transmit the recorded voice command to the server 3000.

In operation 1110, the wearable device 4000 may obtain biometric information of the user. For example, if the wearable device 4000 is a smart band, the wearable device 4000 may sense a heart rate or a body temperature of the user. Additionally, for example, if the wearable device 4000 is a glove or a ring, the wearable device 4000 may sense a blood flow rate at an end of the user's hand. However, the biometric information is not limited thereto, and the wearable device 4000 may obtain various biometric information regarding a brain wave or a motion of the user. Additionally, the wearable device 4000 may sense biometric information of the user for a predetermined period of time or when a predetermined event occurs. In this case, a predetermined period of time or a predetermined event may be preset by the server 3000 or the device 1000.

In operation S1115, the server 3000 may determine a condition for controlling the external apparatus 2000. The server 3000 may analyze information about the voice command and determine a condition for controlling the external apparatus 2000 with respect to the voice command of the user, according to a type of biometric information that may be received from the wearable device 4000 and a type of the external apparatus 2000. Additionally, the server 3000 may determine a condition for controlling the external apparatus 2000 based on condition information collected from at least one selected from the group consisting of the device 1000 and the external apparatus 2000.

The server 3000 may determine an intention of the user, in consideration of the voice command and the biometric information of the user. Additionally, the server may determine a condition for controlling the external apparatus 2000, so as to satisfy the intention of the user. Additionally, the server 3000 may select the external apparatus 2000 that is to be a control target. Additionally, if the condition for controlling the external apparatus 2000 is satisfied, the server 3000 may determine operation of the external apparatus 2000 which is to be controlled by the server 3000.

For example, if a voice command of the user is "I'll be back home within 30 minutes", the wearable device 4000 is a smart band, and one or more external apparatuses 2000 in the house of the user is at least one of an air conditioner 110-2, a heater 110-3, and a temperature sensor 110-1, and if the server 3000 determines that a heart rate of the user is greater than 120 bpm, that calories consumed by the user are greater than 500 kcal, that a moving distance of the user is greater than 3 km, because the user usually feels hot, the server 3000 may determine to set a target temperature of the air conditioner to 18° C.

Additionally, for example, if a voice command of the user is "turn on the air conditioner", the wearable device 4000 is a glove or a ring, and one or more external apparatuses 2000 in the house of the user is at least one of an air conditioner, a heater, and a temperature sensor, and if the server 3000 determines that a blood flow rate at an end of the user's hand is greater than a reference value, that calories consumed by the user are greater than 500 kcal, that a moving distance of the user is greater than 3 km, and that a sensible temperature of the user is greater than 35° C., the server 3000 may determine to set a target temperature of the air conditioner to 18° C.

In operation S1120, the wearable device 4000 may transmit the biometric information of the user to the device 1000. In operation S1125, the device 1000 may transmit the biometric information of the user to the server 3000. The device 1000 may transmit condition information such as a number of steps taken by the user and calories consumed by the user to the server 3000. Additionally, the wearable device 4000 may provide the biometric information of the user for a predetermined period of time or when a predetermined event occurs. In this case, the predetermined period of time or the predetermined event may be preset by the server 3000 or the device 1000.

The device 1000 may receive the voice command, request the wearable device 4000 for the biometric information of the user, and receive the biometric information which is obtained by the wearable device 4000 from the wearable device 4000. Additionally, the device 1000 may simultaneously transmit the voice command and the biometric information to the server 3000. Alternatively, the device 1000 may transmit the biometric information to the server 3000 after the device 1000 transmits the voice command to the server 3000.

Alternatively, the wearable device 4000 may receive the voice command of the user, obtain the biometric information in response to receiving the voice command, and transmit the voice command and the biometric information to the device 1000. Then, the device 1000 may transmit the voice command and the biometric information to the server 3000.

If the wearable device 4000 is included in the device 1000, the device 1000 may receive the voice command of the user, obtain the biometric information in response to receiving the voice command, and transmit the voice command and the biometric information to the server 3000.

In operation S1130, a temperature sensor 110-1 may provide temperature information to the server 3000. The temperature sensor 110-1 in the house may sense a temperature in the house, and provide information about the sensed temperature to the server 3000. The temperature sensor 110-1 may provide the information about the sensed temperature for a predetermined period of time or when a predetermined event occurs. In this case, the predetermined period of time or the predetermined event may be preset by the server 3000 or the device 1000.

In operation S1135, the server 3000 may determine whether the condition for controlling the external apparatus 2000 is satisfied. The server 3000 may determine whether the condition, determined in operation S1115, is satisfied based on the biometric information received from the wearable device 4000 and the condition information received from the at least one selected from the group consisting of the external apparatus 2000 and the device 1000. The server 3000 may determine whether the condition for controlling the external apparatus 2000 is satisfied, in consideration of a heart rate of the user, a blood flow rate at an end of the user's hand, a number of steps taken by the user, a sensible temperature of the user, and a condition inside and outside the house.

Additionally, the server 3000 may determine whether the condition for controlling the external apparatus 2000 is satisfied, by analyzing the biometric information received from the wearable device 4000 and the condition information received from the at least one selected from the group consisting of the external apparatus 2000 and the device 1000.

In operation S1140, the server 3000 may generate control information for controlling the external apparatus 2000. The control information may include control commands with respect to the external apparatus 2000 and the device 1000. The control commands may be arranged according to a certain order. For example, if an operation of the external apparatus 2000 to be controlled by the server 3000 is an 'operation of setting a target temperature of an air conditioner to 18° C.', the server 3000 may generate control information for controlling the air conditioner, by arranging a control command for turning a power of the air conditioner on and a control command for setting a target temperature of the air conditioner to 18° C.

In operation S1145, the server 3000 may provide the control information to the external apparatus 2000. For example, the server 3000 may provide the control information for setting the target temperature to 18° C. to the air conditioner. The server 3000 may transmit the control information directly to the external apparatus 2000. However, the transmitting of the control information is not limited thereto. The server 3000 may provide the control information to the external apparatus 2000 via the device 1000 or a gateway (not shown).

The server 3000 may update the condition for controlling the external apparatus 2000 and a set value for operation of the external apparatus 2000, based on feedback information of the user with respect to control of the external apparatus 2000. For example, if the air conditioner is controlled to set a set temperature to 18° C. when a sensible temperature of the user is 35° C. and the user changes the set temperature of the air conditioner to 22° C. within a predetermined period of time after the user is back home, the air conditioner may transmit the set temperature changed by the user to the server 3000. Thus, the server 3000 may change a set value for 'setting a set temperature of the air conditioner to 18° C. when a sensible temperature is 35° C.' to a set value for 'changing a set temperature of the air conditioner to 22° C. when a sensible temperature is 35° C.'. Then, if a sensible temperature of the user is 35° C. when the user gives a command such as "I'll be back home within 30 minutes", the server 3000 may generate and transmit a control command for setting a temperature to 22° C. to the air conditioner, instead of transmitting a control command for setting a temperature to 18° C. to the air conditioner.

FIG. 12 is a schematic diagram showing an example of an operation table of the device 1000 for controlling the external apparatus 2000 based on biometric information, according to one or more exemplary embodiments.

Referring to FIG. 12, according to one or more exemplary embodiments, the operation table may include a user voice command field 120, a biometric information obtainer field 121, a condition information field 122, a biometric information field 123, an external apparatus controlling condition field 124, an operation field 125, and a control target apparatus field 126.

Information indicating a voice command of a user may be written to the user voice command field 120. Information indicating a voice command of the user such as 'I'll be back within 30 minutes' or 'turn on the air conditioner' may be written to the user voice command field 120.

An identification value or a type of the wearable device 4000 or the device 1000 which may obtain biometric information of the user may be written to the biometric information obtainer field 121. For example, a smart band, a glove, or a ring may be written to the biometric information obtainer field 121.

Information indicating a type of condition information which may be used to determine a condition for controlling the external apparatus 2000 or determine whether a condition for controlling the external apparatus 2000 is satisfied may be written to the condition information field 122. For example, information such as a temperature in a house or a location of the device 1000 may be written to the condition information field 122.

A type of biometric information that may be obtained from the wearable device 4000 may be written to the biometric information field 123. A heart rate, a blood flow rate at an end of a hand, and calorie consumption may be written to the biometric information field 123.

Information indicating a condition for controlling the external apparatus 2000 may be written to the external apparatus controlling condition field 124. For example, a condition such as 'a heart rate: greater than 120 bpm, calorie consumption: 500 kcal, and a moving distance: greater than 3 km' may be written to the external apparatus controlling condition field 124.

Information about operation of the external apparatus 2000 which is to be controlled when the condition for controlling the external apparatus 2000 is satisfied may be written to the operation field 125. Information such as 'air conditioner power on, temperature set to 18° C.' may be written to the operation field 125.

An identification value of the external apparatus 2000 that is to be controlled by the server 3000 may be written to the control target apparatus field 126.

Figure 13:
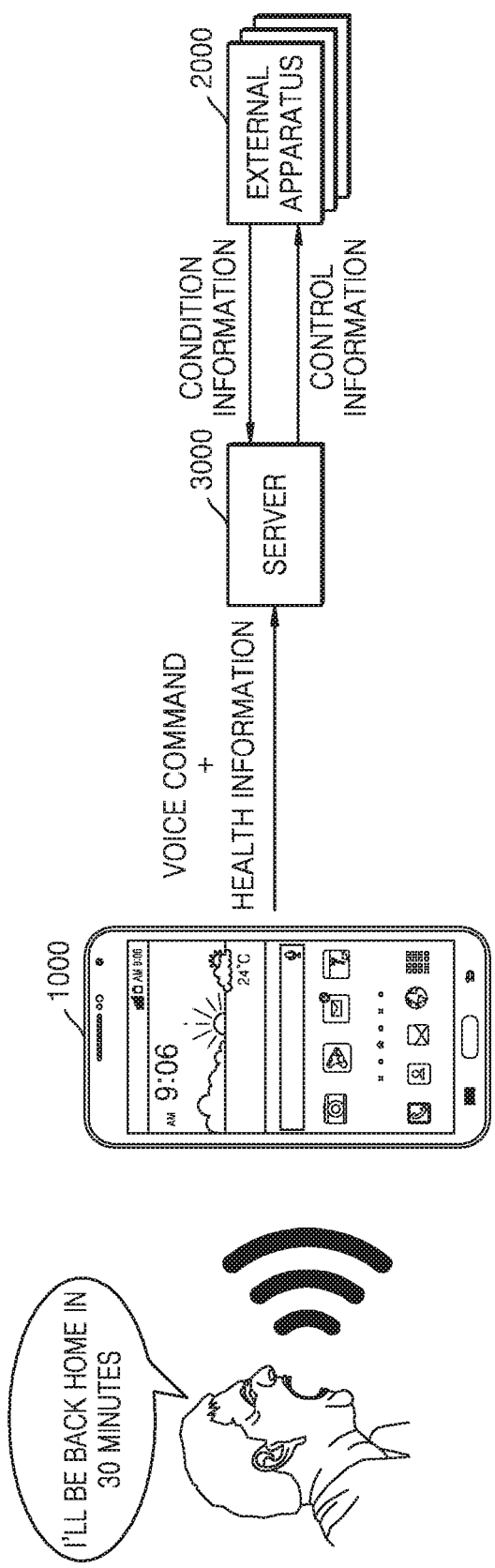
FIG. 13 is a schematic diagram showing an example of controlling an external apparatus based on a voice command and biometric information of a user, which is performed by a server, according to one or more exemplary embodiments.

FIG. 13 is a schematic diagram showing an example of controlling the external apparatus 2000 based on a voice command and biometric information of a user, which is performed by the server 3000, according to one or more exemplary embodiments.

Referring to FIG. 13, the device 1000 may receive a user input of a voice command and a user input of setting a health state of the user. Additionally, the device 1000 may transmit a voice command and health information to the server 3000. The health information of the user may be information regarding a health state of the user, and include information about a name of a disease, a taste, an age, a height, or a weight of the user. The health information of the user may be used to determine a health state of the user.

The server 3000 may receive a voice command and health information from the device 1000, and receive condition information from the external apparatus 2000. In this case, the external apparatus 2000 may be, for example, an apparatus located in a house of the user. Additionally, the server 3000 may receive health information of the user from a hospital server (not shown). In this case, the server 3000 may obtain an authority for accessing the health information of the user which is stored in the hospital server (not shown).

Then, the server 3000 may generate a control command for controlling the external apparatus 2000 in consideration of the voice command of the user, the health information of the user, and a condition of the external apparatus 2000, and transmit the generated control command to the external apparatus 2000.

Thus, the server 3000 may control the external apparatus 2000 according to a voice command of the user, in consideration of the health state of the user.

For example, if the user inputs health information indicating 'asthma' to the device 1000 and inputs a voice command saying "I'll be back home within 30 minutes", the server 3000 may receive health information and voice command information from the device 1000, and thus, analyze an intention of the user. Additionally, the server 3000 may generate a control command for selecting an air purifier 140-4 (see FIG. 14) from among one or more external apparatuses 2000 located in the house and operating the air purifier 20 minutes before the user is back home. Additionally, the server 3000 may transmit the generated control command to the air purifier. In this case, the user may additionally input another piece of health information to the device 1000, and a plurality of pieces of health information may be used by the server 3000.

Figure 14:
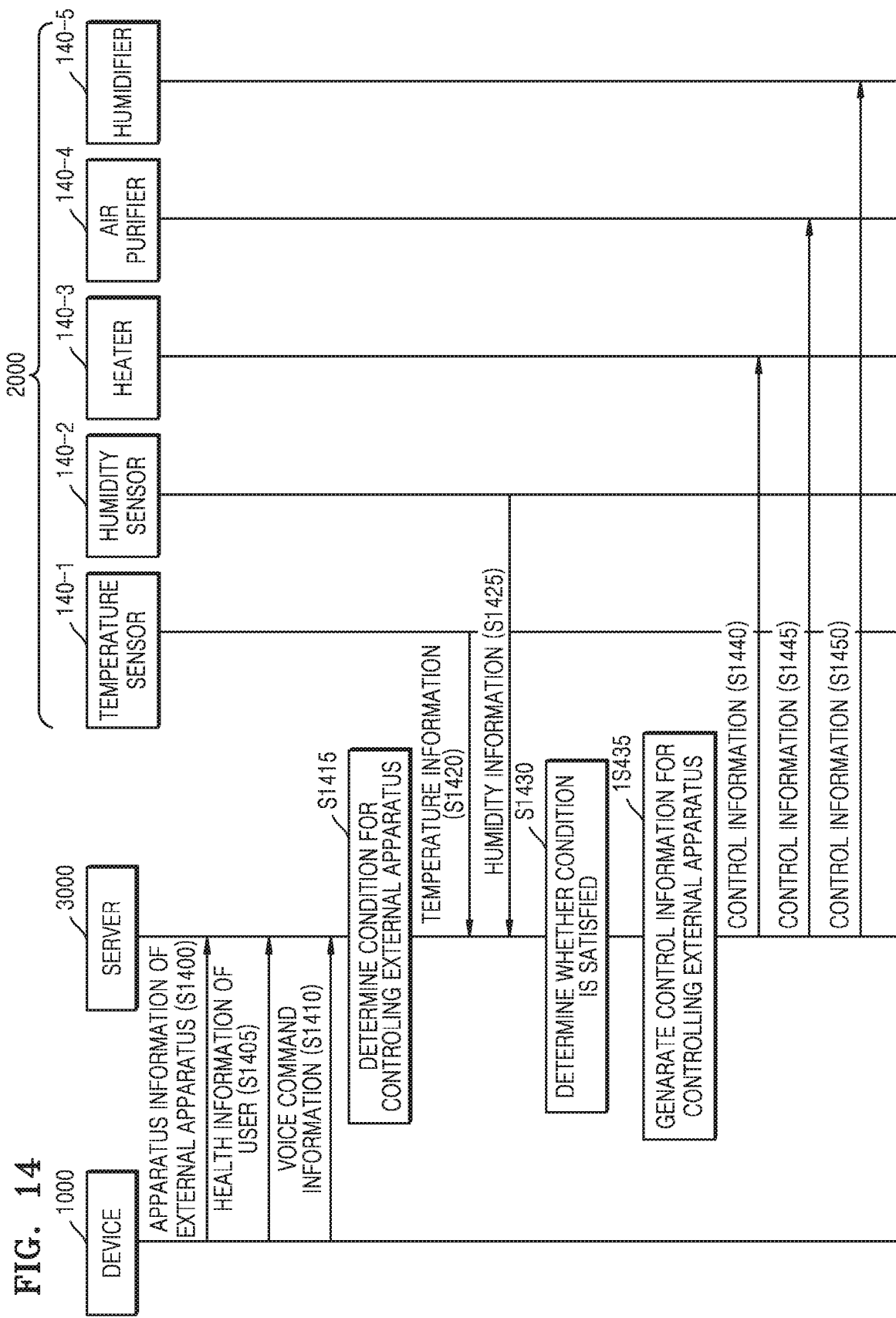
FIG. 14 is a flowchart of a method of controlling the external apparatus according to a voice command of a user in consideration of health information about the user, which is performed by a server, according to one or more exemplary embodiments.

FIG. 14 is a detailed flowchart of a method of controlling the external apparatus 2000 according to a voice command of a user in consideration of health information about the user, which is performed by the server 3000, according to one or more exemplary embodiments.

In operation S1400, the device 1000 may provide apparatus information of the external apparatus 2000 to the server 3000. The device 1000 may provide the apparatus information of the external apparatus 2000, located inside or outside a house of the user, to the server 3000. The apparatus information of the external apparatus 2000, provided to the server 3000 by the device 1000, may be used to set a condition for controlling the external apparatus 2000.

In operation S1405, the device 1000 may provide health information of the user to the server 3000. The device 1000 may display a graphical user interface (GUI) for receiving an input of the health information on a screen of the device 1000, and the user may input a health state of the user to the device 1000 via the displayed GUI.

In operation S1410, the device 1000 may provide voice command information to the server 3000. The device 1000 may record a voice command of the user, and transmit the recorded voice command to the server 3000. However, the providing of the voice command information is not limited thereto. The device 1000 may convert the recorded voice command into text and provide the text, obtained by the converting, to the server 3000. For example, the device 1000 may provide information indicating a voice command of the user such as "I'll be back home within 30 minutes" to the server 3000.

In operation S1410, the device 1000 is described as recording a voice command and transmitting the recorded voice command to the server 3000. However, embodiments are not limited thereto. The wearable device 4000 may record a voice command of the user, and transmit the recorded voice command to the device 1000. Then, the device 1000 may transmit the recorded voice command to the server 3000. Alternatively, the wearable device 4000 may record a voice command and transmit the recorded voice command to the server 3000.

In operation S1415, the server 3000 may determine a condition for controlling the external apparatus 2000. The server 3000 may analyze information about the voice command and determine a condition for controlling the external apparatus 2000 with respect to the voice command of the user, according to a type of the external apparatus 2000 and a health state of the user. Additionally, the server 3000 may determine a condition for controlling the external apparatus 2000 based on condition information collected from at least one selected from the group consisting of the device 1000 and the external apparatuses 2000.

The server 3000 may determine an intention of the user, in consideration of the voice command and the biometric information of the user. Additionally, the server 3000 may determine a condition for controlling the external apparatus 2000, so as to satisfy the intention of the user.

Additionally, the server 3000 may select the external apparatus 2000 that is to be a control target, in consideration of a condition inside or outside the house. Additionally, if the condition for controlling the external apparatus 2000 is satisfied, the server 3000 may determine operation of the external apparatus 2000 that is to be controlled by the server 3000. For example, the server 3000 may determine the external apparatus 2000 that is to be a control target and operation of the external apparatus 2000. In this case, an optimum environment value in the house according to a season and a temperature outside the house may be preset.

For example, if a voice command of the user is 'I'll be back home within 30 minutes', a health state of the user is 'asthma', and one or more of the external apparatuses 2000 in the house of the user include an air conditioner (see FIG. 11), a heater, an air purifier, a temperature sensor, or a humidity sensor, and if the server 3000 determines that the user is near the house, the server 3000 may determine to turn on the power of the air purifier.

Additionally, for example, if a voice command of the user is 'I'll be back home within 30 minutes', a health state of the user is 'atopy, a current season is 'summer', and one or more of the external apparatuses 2000 at the user's home include at least one of an air conditioner, a heater, an air purifier, a humidifier, a dehumidifier, a temperature sensor, and a humidity sensor, and if the server 3000 determines that a temperature in the house is greater than 30° C. and humidity in the house is less than 50%, the server 3000 may determine to set a temperature of the air conditioner to 27° C., and a humidity level of a dehumidifier or a humidifier 140-5 to 55%.

Additionally, for example, if a voice command of the user is 'I'll be back home within 30 minutes', a health state of the user is 'allergic rhinitis', a current season is winter, and one or more of the external apparatuses 2000 at the user's home include at least one of an air conditioner, a heater, an air purifier, a dehumidifier, a temperature sensor, and a humidity sensor, and if the server 3000 determines that a temperature in the house is greater than 15° C. and humidity in the house is less than 30%, the server 3000 may determine to set a temperature of the heater 140-3 to 20° C., and a humidity level of a dehumidifier to 40%.

Additionally, the server 3000 may store set values for an optimum indoor temperature and optimum indoor humidity for a general adult according to seasons. Since a heat retention rate of clothes worn by people varies depending on seasons and temperature and humidity are associated with a person's comfort, optimum humidity may vary depending on a change in an optimum temperature. For example, in spring and fall, an optimum temperature may range from 19° C. to 23° C., and optimum humidity may be 50%. In summer, an optimum temperature may range from 24° C. to 27° C., and optimum humidity may be 60%. In winter, an optimum temperature may range from 18° C. to 21° C., and optimum humidity may be 40%. Additionally, the set values for an optimum indoor temperature and an optimum indoor humidity for a general adult according to seasons may be used for the server 3000 to determine a condition for controlling the external apparatus 2000 and operation of the external apparatus 2000.

Additionally, an optimum temperature and an optimum humidity for the user may be different from an optimum temperature and an optimum humidity for general adults, according to characteristics of the user (for example, the user's age, gender, height, weight, chronic disease, and condition). For example, if the season is summer and a disease of the user is atopy, an optimum indoor temperature for the user may be set to 20° C., and optimum humidity may be set to 55%.

For example, if a user who is an atopic patient inputs a voice command saying "I'll be back home within 30 minutes" in summer, the server 3000 may analyze an intention of the user in consideration of the voice command saying "I'll be back home within 30 minutes". Additionally, the server 3000 may select an air conditioner and a dehumidifier from among one or more external apparatuses 2000, in consideration of the intention of the user, 'summer', and 'atopy', and generate control information so as to set a temperature of the air conditioner to 20° C. and a humidity level of the dehumidifier to 55%, 20 minutes before the user arrives at home.

Additionally, for example, if a season is 'winter' and a health state of the user is 'allergic rhinitis', an optimum indoor humidity for the user may be set to 50% so that the optimum indoor humidity for the user is higher than optimum humidity for general adults. Accordingly, if a user who suffers from allergic rhinitis inputs a voice command saying "I'll be back home within 30 minutes" in winter, the server 3000 may analyze an intention of the user in consideration of the voice command such that "I'll be back home within 30 minutes". Additionally, the server 3000 may select a heater and a dehumidifier from among one or more external apparatuses 2000 in a house of the user, in consideration of the intention of the user, 'winter', and 'atopy', and generate control information so as to set a temperature of the air conditioner to 20° C. and a humidity level of the dehumidifier to 55%, 20 minutes before the user arrives home.

The server 3000 may use various sensing values received from the external apparatus 2000 to determine a condition for controlling the external apparatus 2000 and operation of the external apparatus 2000. Additionally, various set values for the condition for controlling the external apparatus 2000 and operation of the external apparatus 2000 may be stored according to a season, a health state of the user, biometric information of the user, or a condition inside or outside the house.

In operation S1420, a temperature sensor 140-1 in the house may provide temperature information to the server 3000. The temperature sensor 140-1 in the house may sense a temperature in the house, and provide temperature information, obtained by the sensing, to the server 3000. The temperature sensor 140-1 may provide the temperature information for a predetermined period of time or when a predetermined event occurs. In this case, the predetermined period of time or the predetermined event may be preset by the server 3000 or the device 1000.

In operation S1425, a humidity sensor 140-2 in the house may provide humidity information to the server 3000. The temperature sensor 140-1 in the house may sense a temperature in the house, and provide temperature information, obtained by the sensing, to the server 3000. The humidity sensor 140-2 may provide humidity information for a predetermined period of time or when a predetermined event occurs. In this case, the predetermined period of time or the predetermined event may be preset by the server 3000 or the device 1000.

In operation S1430, the server 3000 may determine whether the condition for controlling the external apparatus 2000 is satisfied. The server 3000 may determine whether the condition, determined in operation S1415, is satisfied based on a health state of the user and the condition information collected from at least one selected from the group consisting of the device 1000 and the external apparatuses 2000.

In operation S1435, the server 3000 may generate control information for controlling the external apparatus 2000. The control information may include control commands with respect to the external apparatus 2000 and the device 1000. The control commands may be arranged according to a certain order. For example, if operation of the external apparatus 2000 to be controlled by the server 3000 is 'operation of setting a temperature of an air conditioner to 27° C. and setting a humidity level of the dehumidifier to 55%', the server 3000 may generate control information for controlling the air conditioner and the dehumidifier, by arranging a control command for turning on a power of the air conditioner, a control command for setting a target temperature of the air conditioner to 27° C., a control command for turning on the dehumidifier, and a control command for setting a target humidity level of the dehumidifier to 55%.

In operations S1440, S1445, and S1450, the server 3000 may provide the control information to the external apparatus 2000. The server may transmit the control information directly to the external apparatus 2000. However, the transmitting of the control information is not limited thereto. The server 3000 may provide the control information to the external apparatus 2000 via the device 1000 or a gateway (not shown).

FIG. 15 is a schematic diagram showing an example of an operation table of the device 1000 for controlling the external apparatus 2000 based on a health state of a user, according to one or more exemplary embodiments.

Referring to FIG. 15, according to one or more exemplary embodiments, the operation table may include a user voice command field 150, a user health state field 151, a condition information field 152, an external apparatus controlling condition field 153, an operation field 154, and a control target apparatus field 155.

Information indicating a voice command of a user may be written to the user voice command field 150. Information indicating a voice command of the user saying 'I'll be back within 30 minutes' or 'turn on the air conditioner' may be written to the user voice command field 150.

Information indicating a health state of the user may be written to the user health state field 151. The device 1000 may display a GUI for setting a health state of the user on a screen of the device 1000, and set a health state of the user based on a user input via the GUI. Additionally, information about the set health state may written to the user health state field 151. Information such as 'asthma', 'atopy', or 'allergic rhinitis' may be written to the user health state field 151.

Information indicating a type of condition information which may be used to determine a condition for controlling the external apparatus 2000 or determine whether a condition for controlling the external apparatus 2000 is satisfied may be written to the condition information field 152. For example, information such as a temperature in a house, humidity in the house, or a location of the device 1000 may be written to the condition information field 152.

Information indicating a condition for controlling the external apparatus 2000 may be written to the external apparatus controlling condition field 153. A condition such as 'a location of the user: near home', 'a temperature in the house: greater than 30° C.', or 'humidity in the house: less than 50%' may be written to the external apparatus controlling condition field 153.

Information about operation of the external apparatus 2000 which is to be controlled when the condition for controlling the external apparatus 2000 is satisfied may be written to the operation field 154. Information such as 'air purifier power on, air conditioner power on, temperature set to 27° C., dehumidifier power on, or humidity level set to 55%' may be written to the operation field 125.

An identification value of the external apparatus 2000 that is to be controlled by the server 3000 may be written to the control target apparatus field 155.

Figure 16:
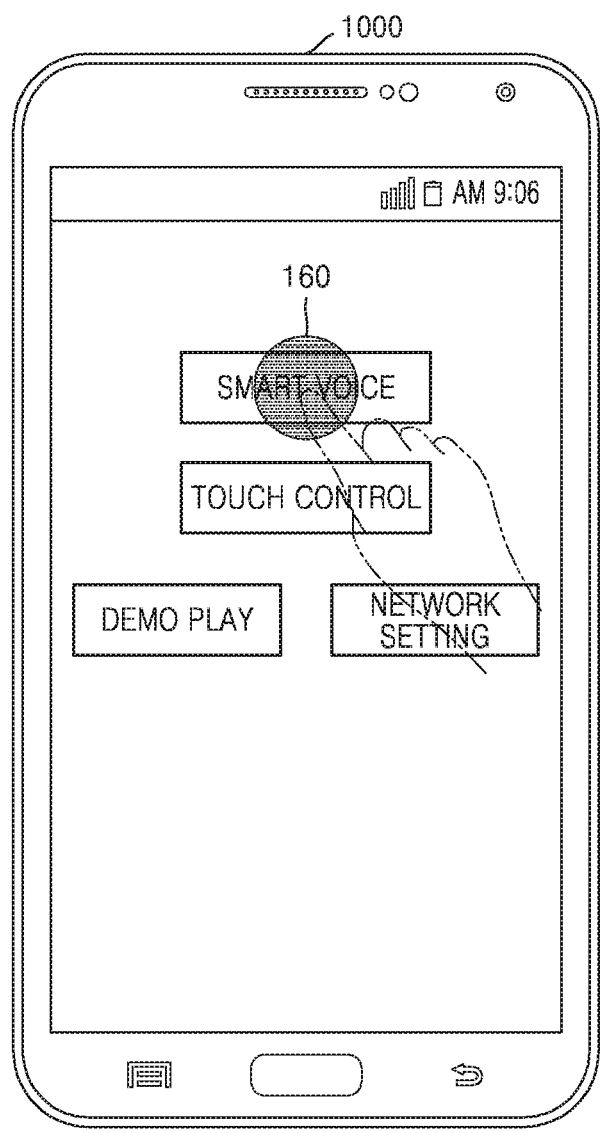
FIGS. 16 and 17 are schematic diagrams showing an example of receiving a voice command of a user, which is performed by a device, according to one or more exemplary embodiments.
Figure 17:
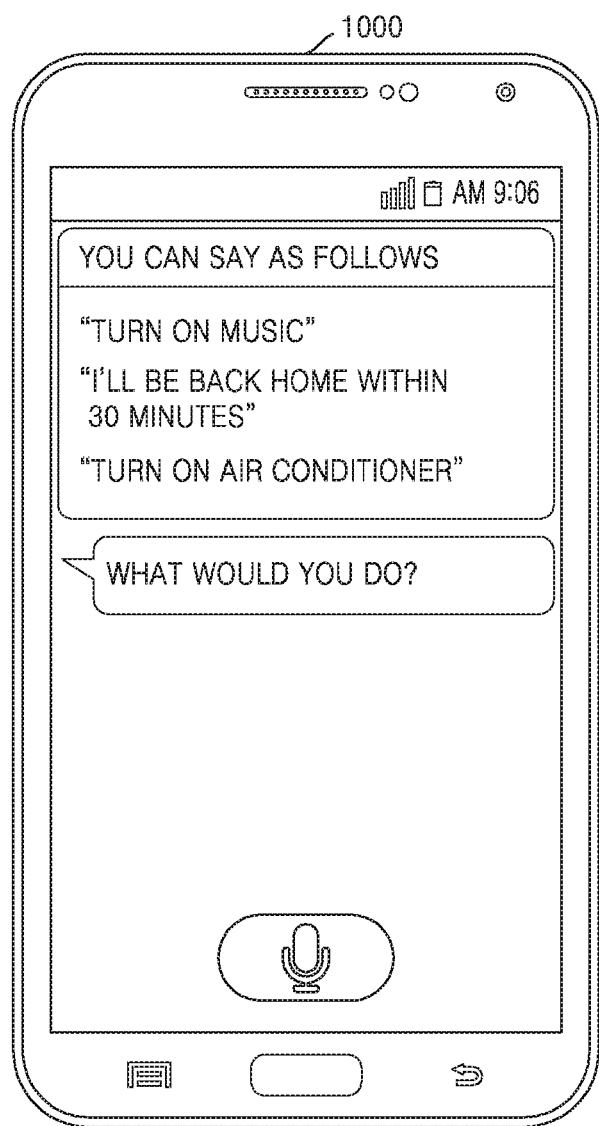

FIGS. 16 and 17 are schematic diagrams showing an example of receiving a voice command of a user, which is performed by the device 1000, according to one or more embodiments.

Referring to FIG. 16, the user may execute a voice recognition application installed on the device 1000, and touch a button 160 for inputting a voice command on an execution screen of the voice recognition application.

Referring to FIG. 17, as the button 160 for inputting a voice command is touched, the device 1000 may display a GUI for guiding a voice input of the user on a screen of the device 1000. Then, the user may input a voice command to the device 1000 via the displayed GUI.

Figure 18:
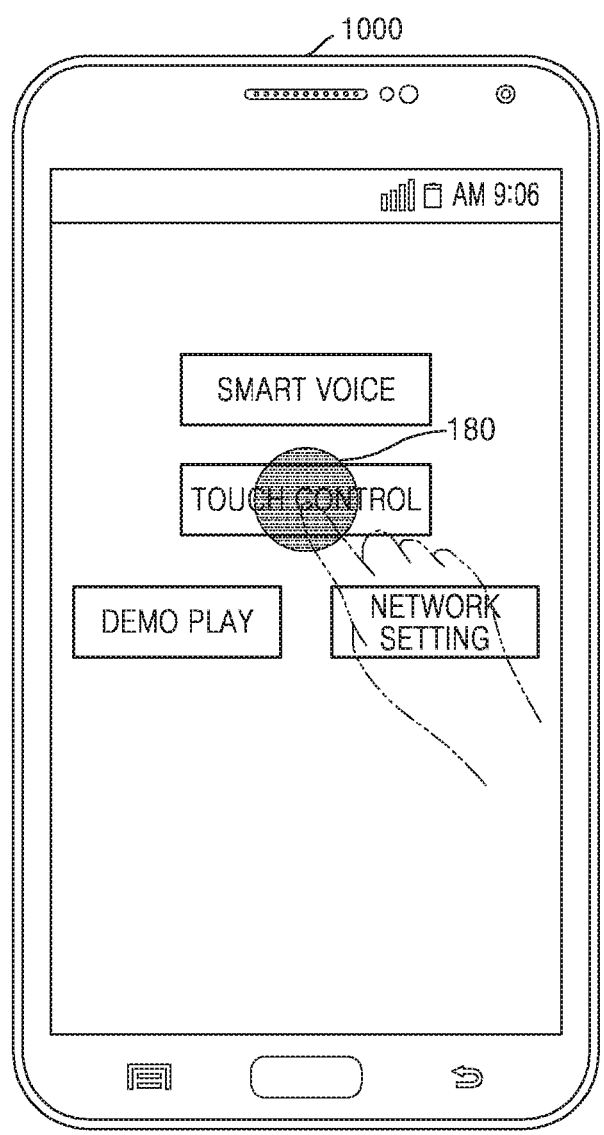
FIGS. 18, 19, 20, 21, and 22 are schematic diagrams showing an example of receiving a user input of health information of a user, which is performed by a device, according to one or more exemplary embodiments.
Figure 19:
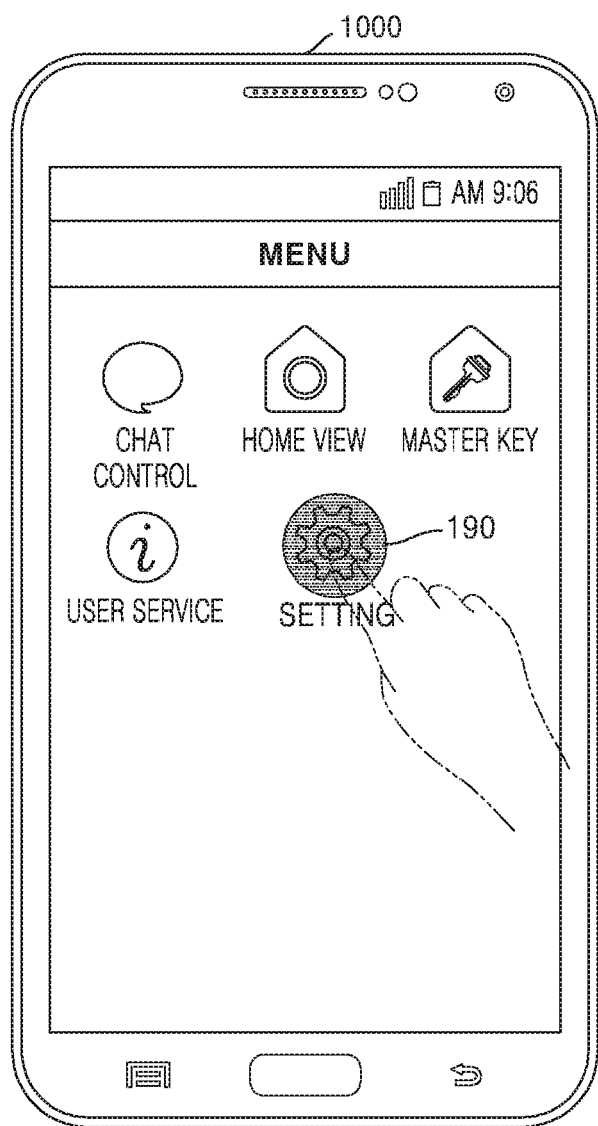
Figure 20:
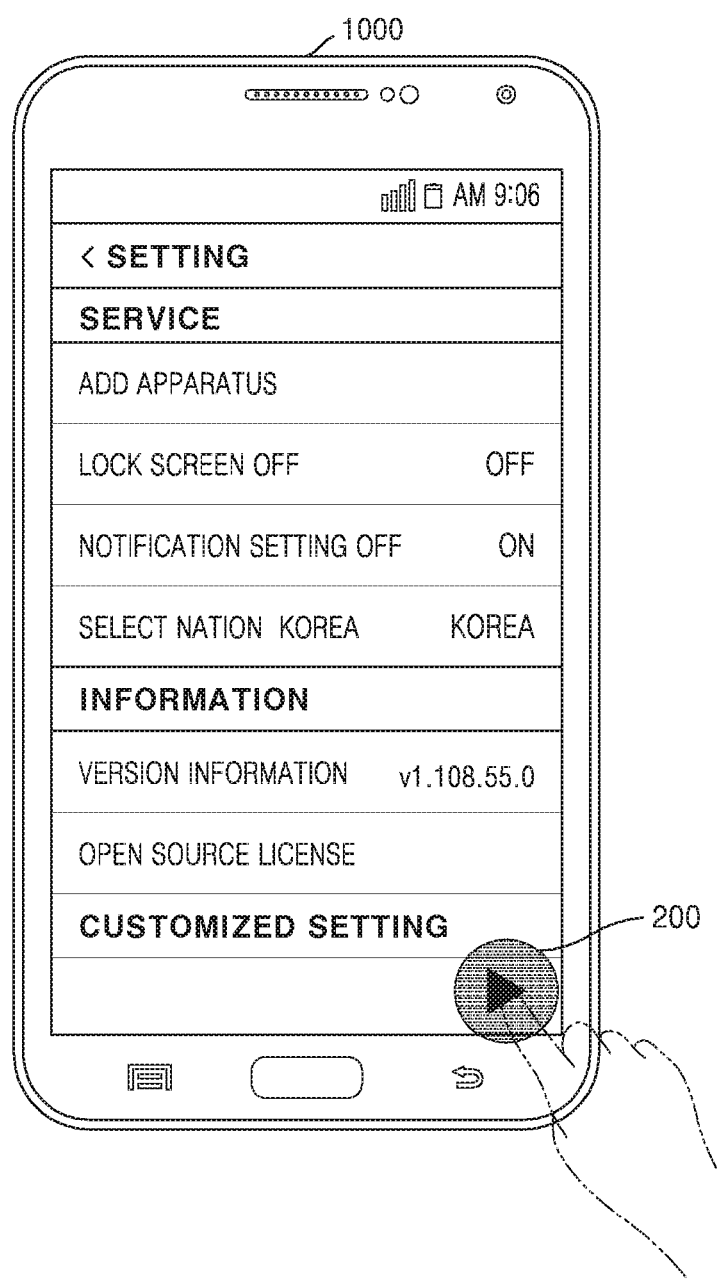

FIGS. 18, 19, and 20 are schematic diagrams showing an example of receiving a user input of health information of a user, which is performed by the device 1000, according to one or more exemplary embodiments.

Referring to FIGS. 18 through 20, the user may execute a voice recognition application installed on the device 1000, and sequentially touch buttons 180, 190 and 200 for inputting health information of the user on an execution screen of the voice recognition application.

Figure 21:
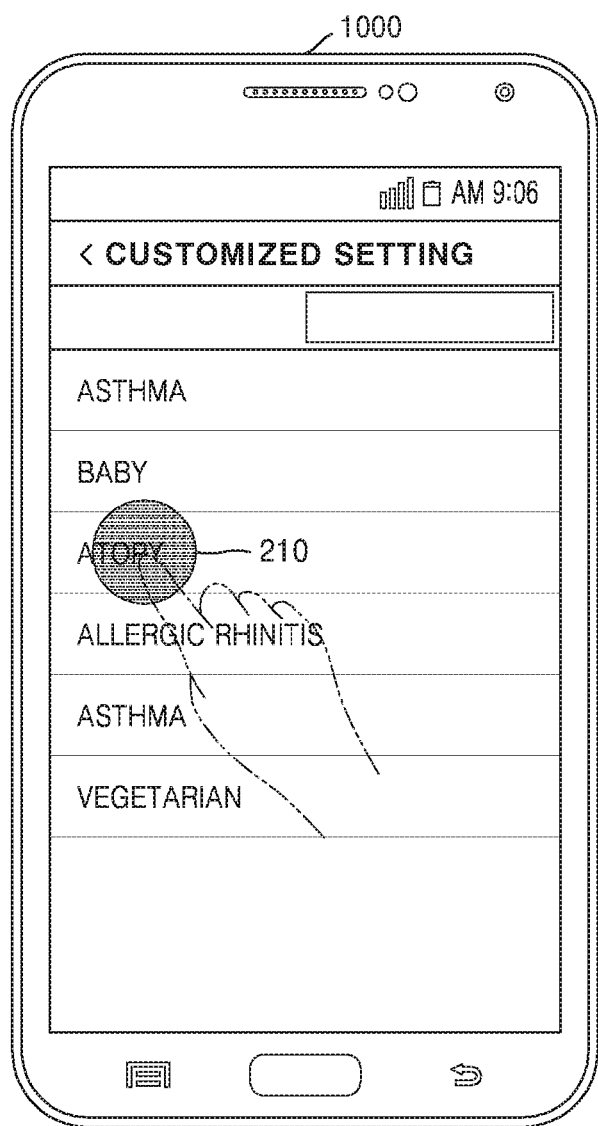

Referring to FIG. 21, as the buttons 180 through 200 for inputting health information are sequentially touched, the device 1000 may display a selection menu for selecting a health state of the user on a screen of the device 1000. The selection menu for selecting a health state of the user may include items such as asthma, a baby, atopy 210, allergic rhinitis, asthma, or a vegetarian. For example, the user may select the atopy 210 from the selection menu.

Figure 22:
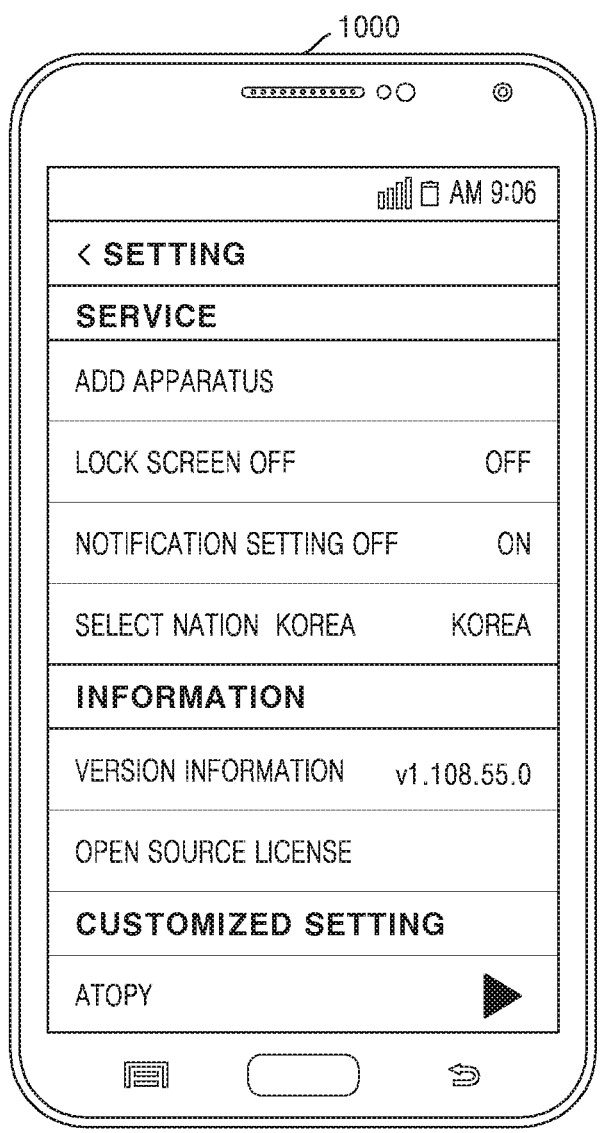

Referring to FIG. 22, as the atopy 210 is selected from the selection menu for selecting a health state of the user, the device 1000 may select a health state of the user as 'atopy'.

Figure 23:
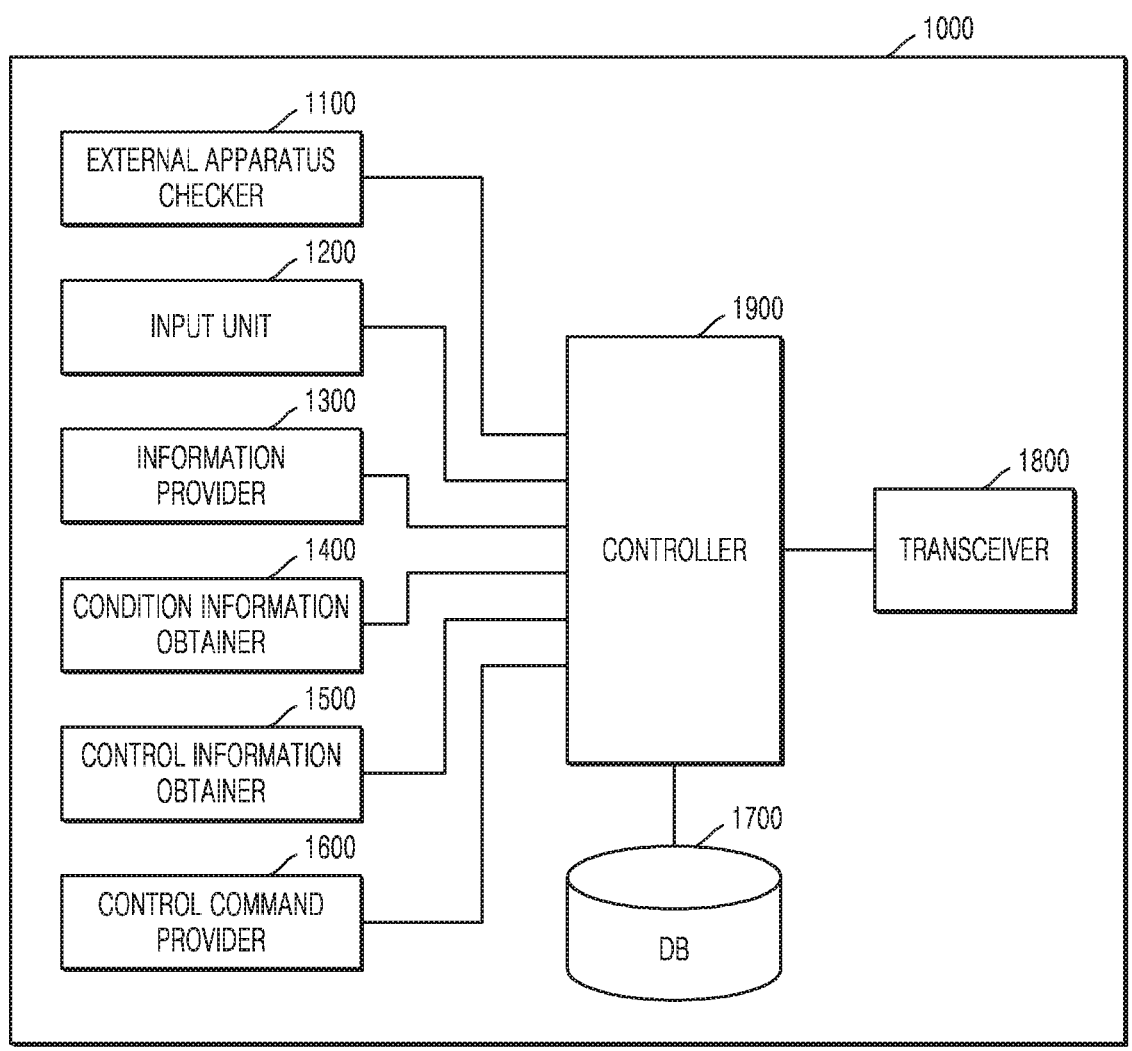
FIG. 23 is a block diagram of a device according to an exemplary embodiment.

FIG. 23 is a block diagram of the device 1000 according to an exemplary embodiment.

As illustrated in FIG. 23, the device 1000 includes an external apparatus checker 1100, an input unit 1200, an information provider 1300, a condition information obtainer 1400, a control information obtainer 1500, a control command provider 1600, a database (DB) 1700, a transceiver 1800, and a controller 1900.

The external apparatus checker 1100 checks the external apparatus 2000 controllable by the device 1000. The external apparatus checker 1100 may check the external apparatus 2000 controllable by the device 1000 from among the external apparatuses connectable with the device 1000. For example, the external apparatus checker 1100 may identify or select the external apparatus 2000 based on criteria, such as connectivity, compatibility, ability to share functionality, etc., with the device 1000.

The external apparatus checker 1100 may receive from the checked external apparatus 2000 apparatus information of the external apparatus 2000, but is not limited thereto. The external apparatus checker 1100 may receive the apparatus information of the external apparatus 2000 from a separate server (not shown). For example, if the device 1000 is connected with the external apparatus 2000 via a home gateway (not shown), the external apparatus checker 1100 may request the home gateway for the apparatus information of the external apparatus 2000. The apparatus information of the external apparatus 2000 may include information about at least one of an identification value of the external apparatus 2000, the type of the external apparatus 2000, and a command used to control the external apparatus 2000.

The input unit 1200 receives a user input about the device 1000, and generates user input information. The user input information may include text data or voice data, but is not limited thereto. Alternatively, the input unit 1200 may generate the user input information by using an email or a text message stored in the device 1000.

The information provider 1300 provides to the server 3000 various types of information for generating control information. The information provider 1300 may provide to the server 3000 at least one of the apparatus information of the external apparatus 2000, the user input information, and condition information.

The condition information obtainer 1400 may obtain the condition information from at least one of the device 1000, a separate server (not shown), and the external apparatus 2000. The condition information obtainer 1400 may obtain the condition information based on the control information obtained by the control information obtainer 1500 to be described below, but is not limited thereto. In order to satisfy a user's intention, the condition information obtainer 1400 may obtain the condition information related to a condition for controlling the external apparatus 2000.

The control information obtainer 1500 obtains the control information for controlling the device 1000 and the external apparatus 2000 according to the user's intention. The control information obtainer 1500 may receive the control information generated by the server 3000, but is not limited thereto. The control information obtainer 1500 may determine the user's intention based on the user input information, may determine the condition for controlling the external apparatus 2000, and may generate the control information. The control information obtainer 1500 may receive information about at least one of the condition for controlling the external apparatus 2000 and the user's intention from the server 3000, and may generate the control information. The control information obtainer 1500 will be described in detail below with reference to FIG. 24.

The control command provider 1600 provides a predetermined control command to the external apparatus 2000 based on the obtained control information. The control information may include a plurality of control commands aligned in a predetermined order, and the control command provider 1600 may provide the plurality of control commands to at least one external apparatus 2000 in a predetermined order.

The DB 1700 stores various types of information to control the device 1000 and the external apparatus 2000 by the device 1000 according to the user's intention.

The transceiver 1800 transmits and receives to and from the external apparatus 2000 and the server 3000 the various types of information needed to control the device 1000 and the external apparatus 2000 by the device 1000 according to the user's intention.

The controller 1900 controls operations of the device 1000, and controls the external apparatus checker 1100, the input unit 1200, the information provider 1300, the condition information obtainer 1400, the control information obtainer 1500, the control command provider 1600, the DB 1700, and the transceiver 1800 in such a way that the device 1000 controls the device 1000 and the external apparatus 2000 according to the user's intention.

Some or all of the external apparatus checker 1100, the input unit 1200, the information provider 1300, the condition information obtainer 1400, the control information obtainer 1500, and the control command provider 1600 may be driven by software modules, but this is not limiting. Some or all of the external apparatus checker 1100, the input unit 1200, the information provider 1300, the condition information obtainer 1400, the control information obtainer 1500, and the control command provider 1600 may be hardware devices.

Also, at least some of the external apparatus checker 1100, the input unit 1200, the information provider 1300, the condition information obtainer 1400, the control information obtainer 1500, and the control command provider 1600 may be included in the controller 1900, and the external apparatus checker 1100, the input unit 1200, the information provider 1300, the condition information obtainer 1400, the control information obtainer 1500, the control command provider 1600, and the controller 1900 may be driven by one processor. However, an exemplary embodiment is not limited thereto.

Figure 24:
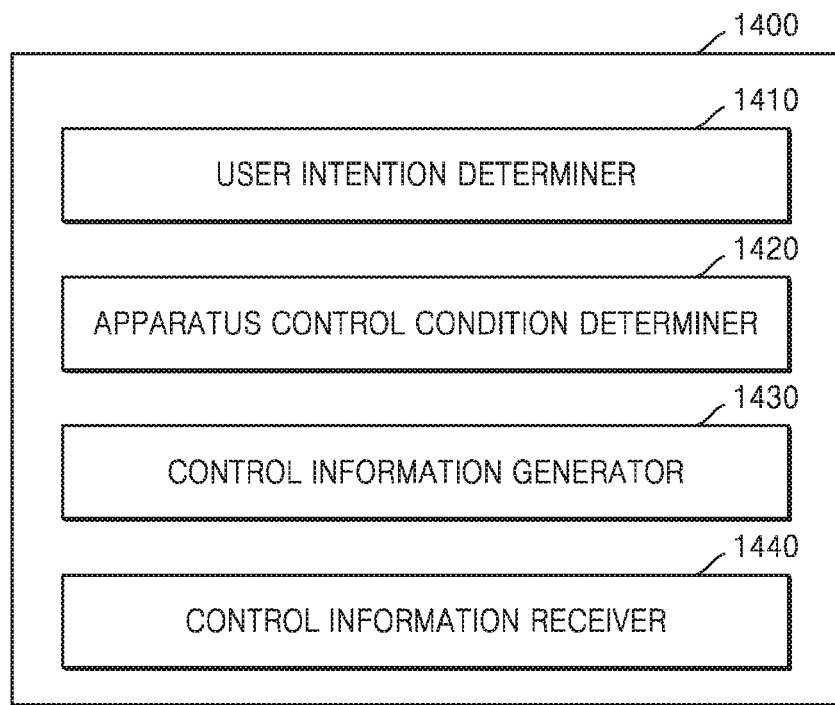
FIG. 24 is a block diagram of a condition information obtainer according to an exemplary embodiment.

FIG. 24 is a block diagram of the condition information obtainer 1400 according to an exemplary embodiment.

As illustrated in FIG. 24, the condition information obtainer 1400 may include a user intention determiner 1410, an apparatus control condition determiner 1420, a control information generator 1430, and a control information receiver 1440.

The user intention determiner 1410 determines a user's intention by analyzing the user input information. For example, the user intention determiner 1410 may use various natural language analysis methods. For example, the device 1000 may analyze text data as the user input information by using natural language processing such as morpheme analysis, syntax analysis, or named entity recognition. If the user input information is voice data, the user intention determiner 1410 may transform the voice data into text data, and may analyze the transformed text data. The user intention determiner 1410 may generate user intention information by analyzing the user input information. For example, if the user input information is "Wake me up at 7:00 if it doesn't rain tomorrow", the user intention determiner 1410 may generate the user intention information including time information such as "tomorrow, 7:00", condition information such as "if it doesn't rain", and operation information such as "wake me up". Alternatively, the user intention determiner 1410 may receive from the server 3000 the user intention information generated by the server 3000.

The apparatus control condition determiner 1420 determines a condition for controlling the external apparatus 2000 based on the user's intention. The apparatus control condition determiner 1420 may determine a condition that has to be satisfied to control operation of the external apparatus 2000 or the device 1000, based on the user intention information. For example, if the user intention information includes time information such as "tomorrow, 7:00" and condition information such as "if it doesn't rain", the apparatus control condition determiner 1420 may determine a time condition such as "tomorrow", a weather condition such as "sunny, cloudy", and a place condition such as "device location" as the condition for controlling the external apparatus 2000. Alternatively, the apparatus control condition determiner 1420 may receive from the server 3000 information about the condition determined the server 3000.

The control information generator 1430 generates control information about the device 1000 and the external apparatus 2000. The control information generator 1430 may determine whether the condition is satisfied, based on the condition information. If the condition determined by the device 1000 is satisfied, the control information generator 1430 may generate the control information for operating the device 1000 or the external apparatus 2000. The control information generator 1430 may generate the control information for operating the device 1000 or the external apparatus 2000, based on operation information, and apparatus information of the external apparatus 2000, which are included in the user intention information. The control information may include control commands about at least one of the external apparatus 2000 and the device 1000, and the control commands may be aligned in a predetermined order.

The control information receiver 1440 may receive from the server 3000 the control information generated by the server 3000.

Figure 25:
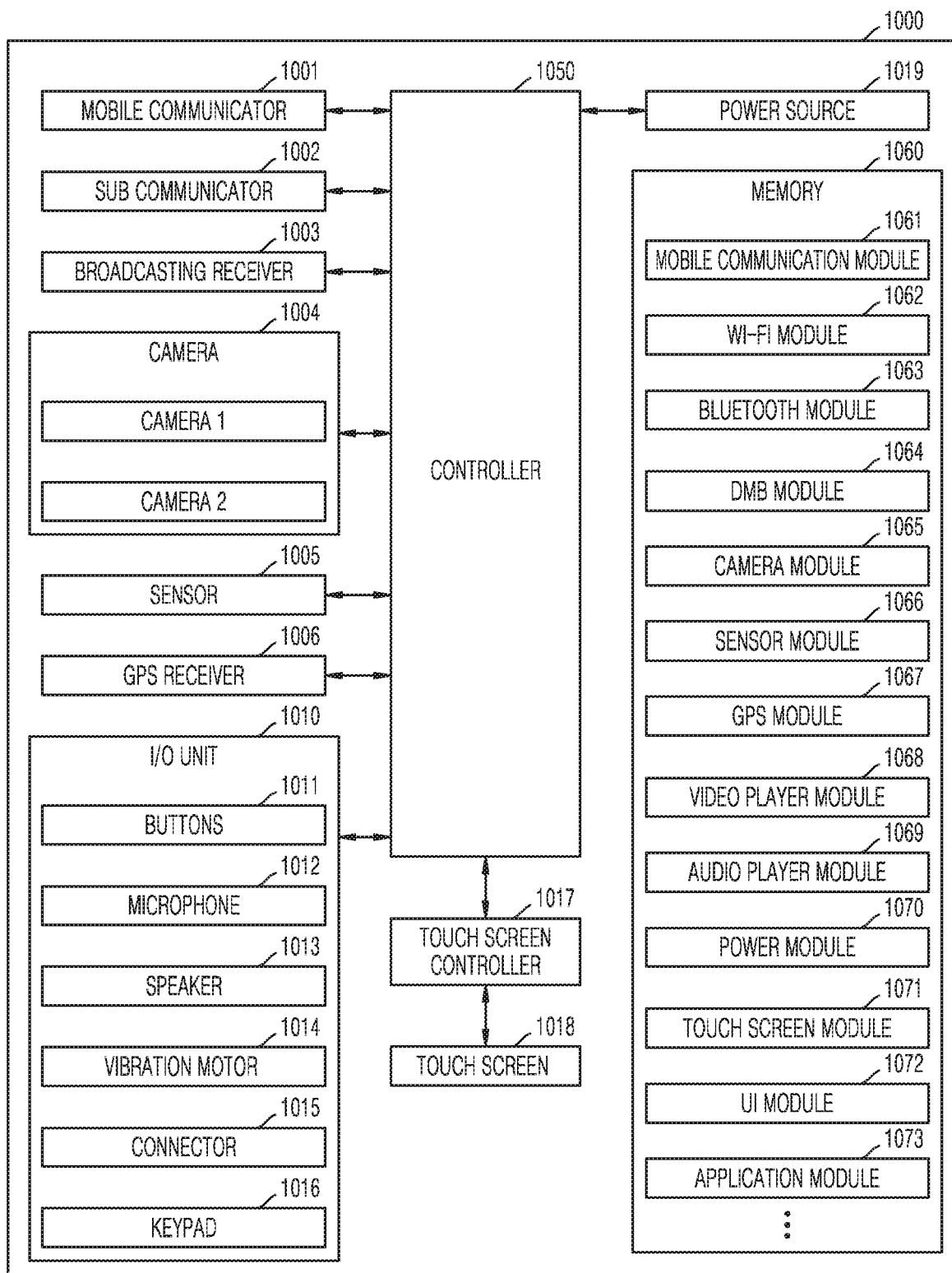
FIG. 25 is a block diagram of a device according to another exemplary embodiment.

FIG. 25 is a block diagram of the device 1000 according to an exemplary embodiment.

A mobile communicator 1001 performs, for example, call setup and data communication with a base station via a cellular network such as a 3G/4G network. A sub communicator 1002 performs a function for short-distance communication such as Bluetooth or NFC. A broadcasting receiver 1003 receives a digital multimedia broadcasting (DMB) signal.

A camera 1004 includes a lens and optical elements for capturing a photo or video.

A sensor 1005 may include a gravity sensor for sensing motion of the device 1000, an illumination sensor for sensing brightness of light, a proximity sensor for sensing proximity of a person, a motion sensor for sensing motion of a person, etc.

A GPS receiver 1006 receives a GPS signal from a satellite. Various services may be provided to a user by using GPS signals.

An input/output (I/O) unit 1010 provides an interface with the external apparatus 2000 or the user, and includes buttons 1011, a microphone 1012, a speaker 1013, a vibration motor 1014, a connector 1015, and/or a keypad 1016.

A touch screen 1018 receives a touch input of the user. A touch screen controller 1017 transmits to a controller 1050 the touch input received by the touch screen 1018. A power supply source 1019 is connected with a battery or an external power source to supply power to the device 1000.

The controller 1050 provides a control command to the external apparatus 2000 by executing programs stored in a memory 1060.

The programs stored in the memory 1060 may be classified into a plurality of modules according to their functions, for example, a mobile communication module 1061, a Wi-Fi module 1062, a Bluetooth module 1063, a DMB module 1064, a camera module 1065, a sensor module 1066, a GPS module 1067, a video player module 1068, an audio player module 1069, a power module 1070, a touch screen module 1071, a user interface (UI) module 1072, and an application module 1073.

Functions of most of the modules would be instinctively understood by one of ordinary skill in the art in view of their names and thus only the application module 1073 will be described here. The application module 1073 may check the external apparatus 2000 connected with the device 1000 by using the mobile communicator 1001 and the sub communicator 1002, and may receive apparatus information from the external apparatus 2000. The application module 1073 may receive a user input by using the I/O unit 1010, and may generate user input information. Furthermore, the application module 1073 may directly obtain condition information via the camera 1004, the sensor 1005, or the GPS receiver 1006, or may receive the condition information from the external apparatus 2000 or a separate server (not shown) by using the mobile communicator 1001 and the sub communicator 1002. Besides, the application module 1073 may obtain control information for controlling the device 1000 and the external apparatus 2000. The application module 1073 may determine the user's intention based on the user input information or may receive user intention information from the server 3000. The application module 1073 may determine a condition for controlling the external apparatus 2000 based on the user's intention, or may receive information about the condition from the server 3000. The application module 1073 may determine whether the condition is satisfied and may generate the control information for controlling the device 1000 and the external apparatus 2000. The application module 1073 may receive the control information generated by the server 3000. Furthermore, the application module 1073 may provide to the external apparatus 2000 a control command included in the control information.

Figure 26:
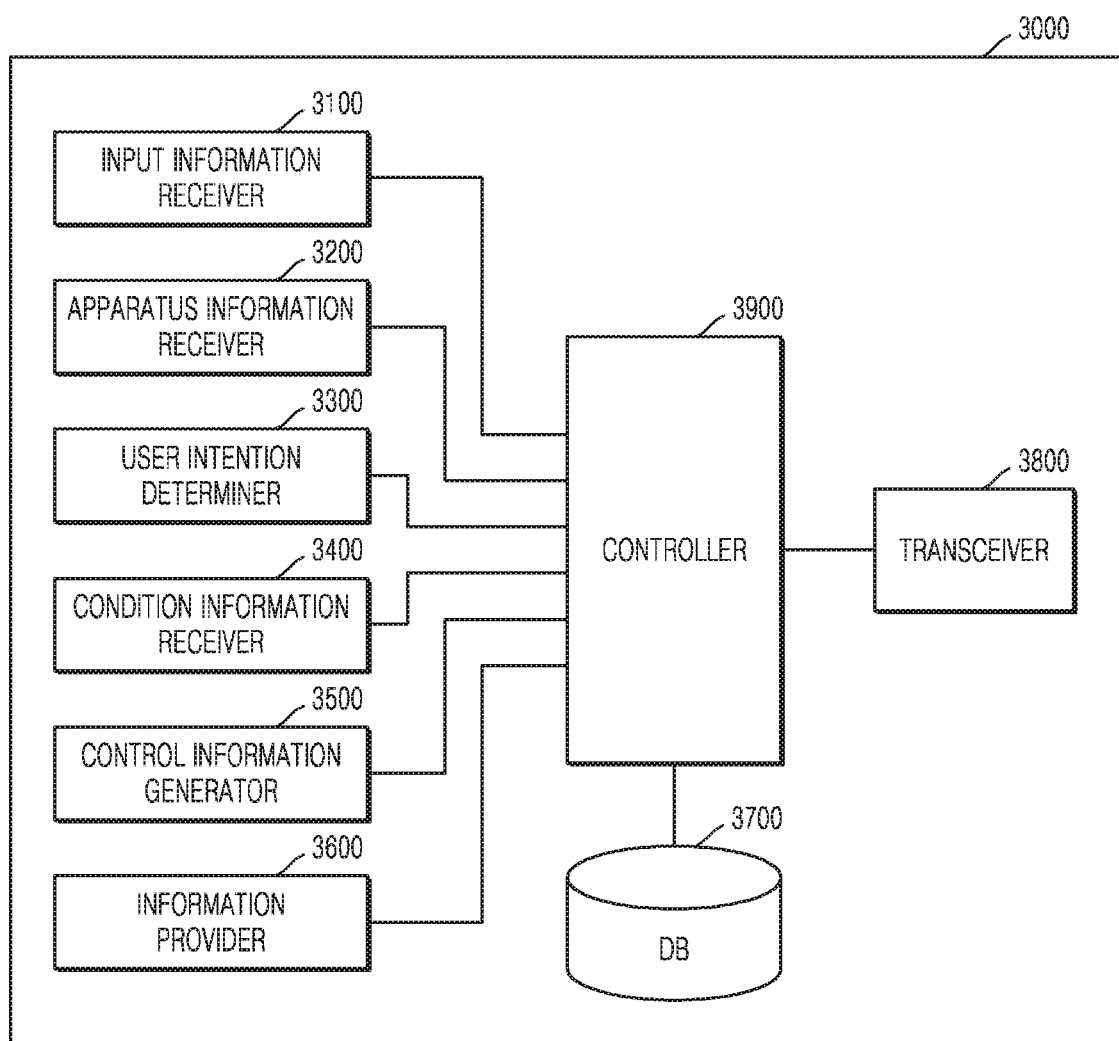
FIG. 26 is a block diagram of a server according to an exemplary embodiment.

FIG. 26 is a block diagram of the server 3000 according to an exemplary embodiment.

As illustrated in FIG. 26, the server 3000 includes an input information receiver 3100, an apparatus information receiver 3200, a user intention determiner 3300, a condition information receiver 3400, a control information generator 3500, an information provider 3600, a DB 3700, a transceiver 3800, and a controller 3900.

The input information receiver 3100 receives user input information from the device 1000. The user input information may include at least one of text data and voice data, but is not limited thereto.

The apparatus information receiver 3200 receives apparatus information of the external apparatus 2000 from the device 1000. The apparatus information may include information including at least one of an identification value of the external apparatus 2000, the type of the external apparatus 2000, and a command used to control the external apparatus 2000.

The user intention determiner 3300 determines a user's intention by analyzing the user input information. For example, the user intention determiner 3300 may use various natural language analysis methods.

The condition information receiver 3400 receives condition information from the device 1000. The condition information receiver 3400 may request the device 1000 for the condition information and may receive from the device 1000 the condition information obtained by the device 1000.

The control information generator 3500 generates control information for controlling the device 1000 and the external apparatus 2000. The control information generator 3500 may generate the control information based on at least one of the user intention information, the apparatus information, and the condition information. The control information generator 3500 may determine the user's intention based on the user input information, may determine the condition for controlling the external apparatus 2000, and may generate the control information.

The information provider 3600 may provide to the device 1000 at least one of the user intention information, and the condition information and the control information for controlling the external apparatus 2000.

The DB 3700 stores various types of information used when the server 3000 generates the control information for operating the device 1000 and the external apparatus 2000 according to the user's intention based on the user input information, and provides the generated control information to the device 1000.

The transceiver 3800 transmits to and receives from the device 1000 the various types of information used when the server 3000 generates the control information for operating the device 1000 and the external apparatus 2000 according to the user's intention based on the user input information, and provides the generated control information to the device 1000.

The controller 3900 controls operations of the server 3000, and controls the input information receiver 3100, the apparatus information receiver 3200, the user intention determiner 3300, the condition information receiver 3400, the control information generator 3500, the information provider 3600, the DB 3700, and the transceiver 3800 in such a way that the server 3000 generates the control information for operating the device 1000 and the external apparatus 2000 according to the user's intention based on the user input information, and provides the generated control information to the device 1000.

Some or all of the input information receiver 3100, the apparatus information receiver 3200, the user intention determiner 3300, the condition information receiver 3400, the control information generator 3500, and the information provider 3600 may be driven by software modules, but are not limited thereto. Some or all of the input information receiver 3100, the apparatus information receiver 3200, the user intention determiner 3300, the condition information receiver 3400, the control information generator 3500, and the information provider 3600 may be hardware devices.

Also, at least some of the input information receiver 3100, the apparatus information receiver 3200, the user intention determiner 3300, the condition information receiver 3400, the control information generator 3500, and the information provider 3600 may be included in the controller 3900, and the input information receiver 3100, the apparatus information receiver 3200, the user intention determiner 3300, the condition information receiver 3400, the control information generator 3500, the information provider 3600, and the controller 3900 may be driven by one processor. However, an exemplary embodiment is not limited thereto.

Exemplary embodiments may be implemented as a medium including computer-executable commands, e.g., a computer-executable program module. A computer-readable medium may be an arbitrary medium that may be accessed by a computer, and may include volatile and nonvolatile media, and detachable and non-detachable media. The computer-readable medium may include a computer recording medium and/or a communication medium. The computer recording medium includes volatile and nonvolatile media, and detachable and non-detachable media that are embodied by using an arbitrary method or technology for storing information such as a computer-readable command, a data structure, a program module, or other data. The communication medium may include a computer-readable command, a data structure, a program module, or other transmission mechanisms, and includes an arbitrary information transmission medium.

Exemplary embodiments may, however, be embodied in many different forms and should not be construed as being limited to the embodiments set forth herein; rather, the described exemplary embodiments are provided so that the disclosure will be thorough and complete, and will fully convey the inventive concept to those of ordinary skill in the art. For example, a single component may be separated into a plurality of components, while a plurality of components may be combined into one component.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. A method for controlling one or more external apparatuses, the method being performed by a mobile device and comprising:
   obtaining an input command of a user;
   identifying the one or more external apparatuses communicable with and controllable by the mobile device, from a plurality of external apparatuses;
   providing the input command and apparatus information of the one or more external apparatuses, to a server;
   receiving, from the server, a control information for controlling a first external apparatus among the one or more external apparatuses, the control information being generated based on whether a control condition for controlling the first external apparatus is satisfied;
   determining whether the control condition is satisfied based on the received control information; and
   transmitting a control command to the first external apparatus based on the determination,
   wherein the control condition for allowing a user-desired operation to be performed according to a user's intention is determined based on the apparatus information and the user's intention, and the user's intention is determined in consideration of the input command.

2. The method of claim 1, further comprising
   obtaining biometric information of the user when the input command is input by the user into the mobile device, and
   wherein the user's intention is determined in consideration of the input command and the biometric information.

3. The method of claim 1, wherein the control command is transmitted to the first external apparatus based on whether another control condition for controlling the first external apparatus among the one or more external apparatuses is satisfied,
   the other control condition is determined based on the apparatus information and the user's intention.

4. The method of claim 1, wherein the input command is generated by the mobile device based on at least one among a text input by the user, a voice of the user, and a gesture of the user.

5. The method of claim 1, wherein the first external apparatus is identified from among the one or more external apparatuses, based on the apparatus information and the user's intention.

6. The method of claim 1, wherein the control information comprises information for checking whether the control condition is satisfied and information for controlling an operation of at least one among the mobile device and the first external apparatus when the control condition is satisfied.

7. The method of claim 1, wherein the control information comprises a plurality of control commands for controlling an operation of at least one among the mobile device and the first external apparatus, the control command being one of the plurality of control commands, and
   the plurality of control commands are executed by at least one among the mobile device and the first external apparatus in a predetermined order.

8. A mobile device comprising:
   a memory configured to store a program; and
   at least one processor configured to control one or more external apparatuses, among a plurality of external apparatuses, by executing the program,
   wherein the program comprises commands which, when executed by the at least one processor, cause the at least one processor to:
   obtain an input command of a user;
   identify the one or more external apparatuses communicable with and controllable by the mobile device, from the plurality of external apparatuses;
   provide the input command and apparatus information of the one or more external apparatuses, to a server;
   receive, from the server, a control information for controlling a first external apparatus among the one or more external apparatuses, the control information being generated based on whether a control condition for controlling the first external apparatus is satisfied;
   determine whether the control condition is satisfied based on the received control information; and
   transmit a control command to the first external apparatus based on the determination,
   wherein the control condition for allowing a user-desired operation to be performed according to a user's intention is determined based on the apparatus information and the user's intention, and the user's intention is determined in consideration of the input command.

9. The mobile device of claim 8, wherein the control command is transmitted to the first external apparatus based on whether another control condition for controlling the first external apparatus among the one or more external apparatuses is satisfied,
   the other control condition is determined based on the apparatus information and the user's intention.

10. The mobile device of claim 8, wherein the input command is generated by the mobile device based on at least one among a text input by the user, a voice of the user, and a gesture of the user.

11. The mobile device of claim 8, wherein the first external apparatus is identified from among the one or more external apparatuses, based on the apparatus information and the user's intention.

12. The mobile device of claim 8, wherein the control information comprises information for checking whether the control condition is satisfied and information for controlling an operation of at least one among the mobile device and the first external apparatus when the control condition is satisfied.

13. The mobile device of claim 8, wherein the control information comprises a plurality of control commands for controlling an operation of at least one among the mobile device and the first external apparatus, the control command being one of the plurality of control commands, and the plurality of control commands are executed by at least one among the mobile device and the first external apparatus in a predetermined order.

14. A computer program product comprising a non-transitory computer-readable storage medium configured to store one or more computer programs including instructions that, when executed by at least one processor, cause the at least one processor to control to perform the method of claim 1.

15. The mobile device of claim 8, the at least one processor obtains biometric information of the user when the input command is input by the user into the mobile device, and wherein the user's intention is determined in consideration of the input command and the biometric information.

\* \* \* \* \*